(12) United States Patent
Liu et al.

(10) Patent No.: US 9,386,769 B2
(45) Date of Patent: Jul. 12, 2016

(54) THIAZOLE METHYLAMINO PYRIDINE COMPOUNDS AND PREPARATION METHOD THEREFOR

(71) Applicant: HUNAN RESEARCH INSTITUTE OF CHEMICAL INDUSTRY CO., LTD., Changsha, Hunan (CN)

(72) Inventors: Aiping Liu, Changsha (CN); Xiaoguang Wang, Changsha (CN); Lian He, Changsha (CN); Xiaoming Ou, Changsha (CN); Minhua Liu, Changsha (CN); Ming Chen, Changsha (CN); Xingping Liu, Changsha (CN); Ming Tang, Changsha (CN); Yeguo Ren, Changsha (CN); Haobin Chen, Changsha (CN)

(73) Assignee: HUNAN RESEARCH INSTITUTE OF CHEMICAL INDUSTRY CO., LTD., Changsha, Hunan (CN)

(*) Notice: Subject to any disclaimer, the term of this patent is extended or adjusted under 35 U.S.C. 154(b) by 0 days.

(21) Appl. No.: 14/369,197

(22) PCT Filed: Oct. 11, 2012

(86) PCT No.: PCT/CN2012/082774
§ 371 (c)(1),
(2) Date: Aug. 27, 2014

(87) PCT Pub. No.: WO2013/097518
PCT Pub. Date: Jul. 4, 2013

(65) Prior Publication Data
US 2015/0051402 A1 Feb. 19, 2015

(30) Foreign Application Priority Data

Dec. 27, 2011 (CN) .......................... 2011 1 0443914

(51) Int. Cl.
*C07D 417/12* (2006.01)
*A01N 43/78* (2006.01)

(52) U.S. Cl.
CPC .............. *A01N 43/78* (2013.01); *C07D 417/12* (2013.01)

(58) Field of Classification Search
CPC ...................................................... C07D 417/12
USPC ...................................................... 546/270.7
See application file for complete search history.

(56) References Cited

U.S. PATENT DOCUMENTS 5,538,976 A * 7/1996 Okada .................. C07D 237/20
514/242

* cited by examiner

*Primary Examiner* — Patricia L Morris
(74) *Attorney, Agent, or Firm* — Raymond Y. Chan; David and Raymond Patent Firm

(57) ABSTRACT

Disclosed are thiazole methylamino pyridine compounds represented by the general formula (I) having fungicidal, insecticidal/acaricidal, and herbicidal activity, the preparation method thereof, the fungicidal, insecticidal/acaricidal, and herbicidal compositions containing the compounds of the present invention, and the use and the method for controlling fungi, insects/acari and weeds of the compounds of the present invention.

5 Claims, No Drawings

THIAZOLE METHYLAMINO PYRIDINE COMPOUNDS AND PREPARATION METHOD THEREFOR

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

1. Field of Invention

The present invention relates to fungicidal, insecticidal/acaricidal and herbicidal thiazole methylamine pyridine compounds, and the preparation method thereof, fungicidal, insecticidal/acaricidal and herbicidal compositions containing the thiazole methylamine pyridine compounds, and the use and method thereof for controlling fungi, pests/mites, and weeds.

2. Description of Related Arts

Heterocyclic compounds, especially thiazoles and pyridines, are important compounds in the medicine chemistry, they have a broad spectrum of biological activities. Although there are many reports related to heterocyclic compounds, especially thiazole heterocyclic compounds or pyridine heterocyclic compounds, it is difficult to find literatures related to thiazole methylamino pyridine compounds.

The control of fungi, pests/mites, and weeds are very important in the process for achieving efficient agriculture. Meanwhile, the control of fungi, pests/mites, and weeds are also very important in forestry, animal husbandry, sideline production, fishery and public health. Although there have been a lot of controllers for fungi, pests/mites and weeds on the market, scientists still need to continuously research on developing new fungicides, insecticides/miticides and herbicides with high efficiency, safety, economy, environmental compatibility and different modes of action, due to the continuous expansion of the market, the resistance of pathogenic bacteria, insects/mites, and weeds, the usage life and economic issues and the increasing emphasis on the environment for all of human.

In order to obtain the compounds with unique mechanisms of action as well as high efficiency and broad spectrum of biological activity, novel thiazole methylamino pyridine compounds represented by the general formula (I) with fungicidal, insecticidal/acaricidal and herbicidal activities, which have not been reported in the literatures, were designed and synthesized by the inventors. Some of these compounds, such as 05, have commercial prospects for exhibiting a potent activity.

SUMMARY OF THE PRESENT INVENTION

A main object of the present invention is to provide the biocidal N-thiazolylmethylpyridin-amine compounds and the isomers thereof represented by the general formula (I):

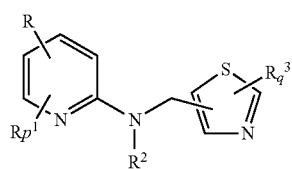

(I)

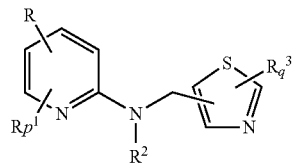

Wherein:
I. R is halogens or nitro group;
II. p is 0, 1, 2 or 3;
III. q is 0, 1 or 2;
IV. $R^1$, $R^2$ and $R^3$ may be the same or different, and they represent:
  (a) hydrogen, halogen, or cyano group;
  (b) alkyl group, alkoxy group, alkylthio group, alkylsulfonyl group, alkylsulfinyl group, alkoxycarbonyl group, alkenyl group, alkenoxy group, alkenylsulfenyl group, alkenylsulfonyl group, alkenylsulfinyl group, alkynyl group, alkynyloxy group, alkynylsulfenyl group, alkynylsulfonyl group, alkynylsulfiny group, cycloalkyl group, cycloalkoxy group, cycloalkylthio group, cycloalkylsulfonyl group, cycloalkylsulfiny, alkylcarbonyl group, aryl group, aryloxy group, arylthio group, aryloxy carbonyl group, arylsulfonyl group, arylsulfinyl group, heteroaryl group, heteroaryloxy group, heteroarylthio group, heteroaryloxycarbonyl group, heteroarylsulfonyl group, or heteroarylsulfinyl group;
  (c) $NR^4R^5$ ($R^4$ and $R^5$ are the same or different, and they represent hydrogen, alkyl group, alkoxy group, alkylthio group, alkylsulfonyl group, alkylsulfinyl group, alkoxycarbonyl group, alkenyl group, alkenoxy group, alkenylsulfenyl group, alkenylsulfonyl group, alkenylsulfinyl group, alkynyl group, alkynyloxy group, alkynylsulfenyl group, alkynylsulfonyl group, alkynylsulfiny group, cycloalkyl group, cycloalkoxy group, cycloalkylthio group, cycloalkylsulfonyl group, cycloalkylsulfiny, alkylcarbonyl group, aryl group, aryloxy group, arylthio group, aryloxy carbonyl group, arylsulfonyl group, arylsulfinyl group, heteroaryl group, heteroaryloxy group, heteroarylthio group, heteroaryloxycarbonyl group, heteroarylsulfonyl group, or heteroarylsulfinyl group);
  (d) As mentioned in IV.(a), IV.(b) or IV.(c), one or more hydrogen atoms in $R^1$, $R^2$ or $R^3$ may be substituted by the same or different following substituent:
    halogens, nitro group, cyano group, alkyl group, alkenyl group, alkynyl group, cycloalkyl group, aryl group, heteroaryl group, alkoxy group, alkylthio group, amino group, alkylamino group, dialkylamino group, halo-alkyl group, alkenoxy group, alkenylsulfenyl group, alkenylamino group, alkenylalkyl group, halo-alkenyl group, alkynyloxy group, alkynylsulfenyl group, alkynylamino group, alkynylalkyl group, halo-alkynyl group, cycloalkoxy group, cycloalkylthio group, cycloalkylamino group, cycloalkylalkyl group, halo-cycloalkyl group, aryloxy group, arylthio group, arylamino group, arylalkyl group, halo-aryl group, heteroaryloxy group, heteroarylthio group, heteroarylamino group, heteroarylalkyl group, or halo-heteroaryl group.
  (e) Aryl group or heteroaryl group mentioned in IV.(a), IV.(b), IV.(c) or IV.(d), may be hydrogenated partially or entirely, and one or two $CH_2$ groups may be substituted with CO.

According to the definition of formula (I), the terms used either alone or in compound words, represent the following substituents generally:
  halogen: represent fluorine, chlorine, bromine or iodine;
  alkyl group: represents a $C_1$-$C_6$ straight-chain or branched-chain alkyl group;

alkoxy group: represents a $C_1$-$C_6$ straight-chain or branched-chain alkoxy group attached to the structure by oxygen atom;

alkylthio group: represents a $C_1$-$C_6$ straight-chain or branched-chain alkylthio group attached to the structure by sulfur atom;

alkenyl group: represents a $C_2$-$C_6$ straight-chain or branched-chain alkenyl group;

alkynyl group: represents a $C_2$-$C_6$ straight-chain or branched-chain alkynyl group;

aryl group: represents a phenyl group or a naphthyl group;

heteroaryl: represents heteroaryl group having up to 10 carbon atoms;

halo-: represents one, a plurality of, or all of the hydrogen atoms are substituted by halogens.

the compounds of the present invention represented by the general formula (I) have geometric isomers (which are represented by trans form E and cis form Z) due to C=C, C≡C or C=N are attached by different substituents, the present invention includes Z form isomers, E form isomers and mixtures thereof in any ratio.

The compounds of the present invention represented by the general formula (I) have stereoisomers (which are represented by R isomer and S isomer) due to carbon atom or nitrogen atom is attached by different substituents, the present invention includes R isomers, S isomers and mixtures thereof in any ratio.

The compounds of the present invention represented by the general formula (I) not only relates to geometric isomers (Z/E) and stereoisomers (R/S), but also relates to the mixtures in any proportion of geometrical isomers (Z/E) and stereoisomers (R/S) thereof.

The N-thiazolylmethylpyridin-amine compounds of the present invention represented by the general formula (I) synthetized by the inventors have a broad spectrum of activities: Some compounds represented by the general formula (I) can be used to control a variety of pests, such as aphids; some compounds represented by the general formula (I) can be used to control mites, such as *tetranychus cinnatarinus* and *panonychus citri*; some compounds represented by the general formula (I) can be used to control diseases caused by the fungi, such as hyphomycetes, phycomycetes, oomycetes, ascomycetes and deuteromycetes. Some compounds represented by the general formula (I) not only can be used to control mites, such as *tetranychus cinnatarinus, panonychus citri* and a variety of pests, such as aphids as well as to control diseases caused by the fungi, such as hyphomycetes, phycomycetes, oomycetes, ascomycetes and deuteromycetes, and some compounds represented by the general formula (I) show very high biological activities and have a very good efficacy at very low use rates. Some compounds represented by the general formula (I) not only have very good activities against *Sclerotonia sclerotiorum* and *Botrytis cinerea*, but also have good activities against *Alternaria alternate, Gibberella zeae* and *phytophthora capsici*. In particular, some compounds represented by the general formula (I) not only have excellent activities against pathogens such as *Sclerotonia sclerotiorum* and *Botrytis cinerea*, but also have excellent activities against undesirable insect pests such as aphids.

The present invention can be explained with the compounds in table 1 and table 2, but the present invention is not limited to the compounds in Table 1 and Table 2. The melting points of the present invention have not been corrected.

TABLE 1

(structure I with $R_p^1$, $R^2$, $R_q^3$, p=q=1)

(structure I-A with R, $R_1^1$, $R^2$, $R_1^2$)

| No. | R | $R_1^1$ | $R^2$ | $R_1^3$ | m.p.(° C.) |
|---|---|---|---|---|---|
| 01 | $NO_2$ | Cl | $CH_2CH_3$ | Cl | 71.4-74.1 |
| 02 | $NO_2$ | H | H | Cl | 93.5-95.8 |
| 03 | $NO_2$ | H | $CH_2CH_3$ | Cl | 90.2-93.6 |
| 04 | $NO_2$ | $OCH_2CH_3$ | $CH_2CH_3$ | Cl | Brown viscous liquid |
| 05 | $NO_2$ | $OCH_3$ | $CH_2CH_3$ | Cl | 64.7-66.6 |
| 06 | $NO_2$ | H | $CH_2CH_2CH_3$ | Cl | 76.9-79.8 |
| 07 | $NO_2$ | $OCH_2CH_2CH_3$ | $CH_2CH_3$ | Cl | Yellow viscous liquid |
| 08 | $NO_2$ | $OCH_3$ | $CH_2CH_2CH_3$ | Cl | Yellow viscous liquid |
| 09 | $NO_2$ | $OCH_2CH_3$ | $CH_2CH_2CH_3$ | Cl | Yellow viscous liquid |
| 10 | $NO_2$ | $OCH_2CH_2CH_3$ | $CH_2CH_2CH_3$ | Cl | Yellow viscous liquid |
| 11 | $NO_2$ | $OCH_2CH_3$ | $CH_2CH_2CH_2CH_3$ | Cl | Yellow viscous liquid |
| 12 | $NO_2$ | Cl | H | Cl | 113.4-114.9 |
| 13 | $NO_2$ | Cl | $CH_3$ | Cl | 125.4-129.8 |
| 14 | $NO_2$ | $OCH_3$ | H | Cl | 150.2-151.0 |
| 15 | $NO_2$ | $NHCH_3$ | H | Cl | 181.1-184.7 |
| 16 | $NO_2$ | $OCH_2CH_3$ | $CH_2CH_3$ | Br | Yellow viscous liquid |
| 17 | $NO_2$ | $OCH_3$ | $CH_3$ | Cl | 122.5-123.8 |
| 18 | $NO_2$ | $SCH_3$ | $CH_2CH_3$ | Cl | Viscous solid |
| 19 | $NO_2$ | $NHCH_2CH_3$ | $CH_3$ | Cl | 170.6-171.3 |
| 20 | $NO_2$ | $NHCH_3$ | $CH_3$ | Cl | 145.7-146.1 |
| 21 | $NO_2$ | $NHCH(CH_3)_2$ | $CH_3$ | Cl | 121.4-123.8 |
| 22 | $NO_2$ | $NHCH_3$ | $CH_2CH_3$ | Cl | 117.6-120.1 |
| 23 | $NO_2$ | $N(CH_3)_2$ | $CH_3$ | Cl | 125.0-127.1 |
| 24 | $NO_2$ | $NHCH_2CH_3$ | $CH_2CH_3$ | Cl | 114.9-116.3 |
| 25 | $NO_2$ | $OCH_2C≡CH$ | $CH_2CH_3$ | Cl | Viscous solid |
| 26 | $NO_2$ | $OCH_2CF_3$ | $CH_2CH_3$ | Cl | Yellow solid |
| 27 | $NO_2$ | $NHCH(CH_3)_2$ | $CH_2CH_3$ | Cl | 86.9-87.8 |
| 28 | $NO_2$ | $N(CH_3)_2$ | $CH_2CH_3$ | Cl | 74.6-78.4 |
| 29 | $NO_2$ | $OCH_2CH=CH_2$ | $CH_2CH_3$ | Cl | Brown solid |
| 30 | $NO_2$ | $OC_6H_5$ | $CH_2CH_3$ | Cl | Brown solid |
| 31 | $NO_2$ | $OCH_2CH_3$ | $CH(CH_3)_2$ | Cl | 78.4-81.1 |
| 32 | $NO_2$ | Cl | $CH_2CH_3$ | Br | 88.7-91.3 |
| 33 | $NO_2$ | $OCH_3$ | $CH_2CH_3$ | Br | Viscous solid |
| 34 | $NO_2$ | $N(CH_2CH_3)_2$ | $CH_2CH_3$ | Cl | Yellow viscous liquid |

TABLE 1-continued

| No | R | $R_1^1$ | $R^2$ | $R_1^3$ | m.p.(° C.) |
|---|---|---|---|---|---|
| 35 | NO₂ | pyrrolidinyl | CH₂CH₃ | Cl | 107.6-108.1 |
| 36 | NO₂ | morpholinyl | CH₂CH₃ | Cl | 117.8-118.7 |
| 37 | Cl | Cl | CH₂CH₃ | Cl | 95.8-96.8 |
| 38 | Cl | OCH₃ | CH₂CH₃ | Cl | Yellow viscous liquid |

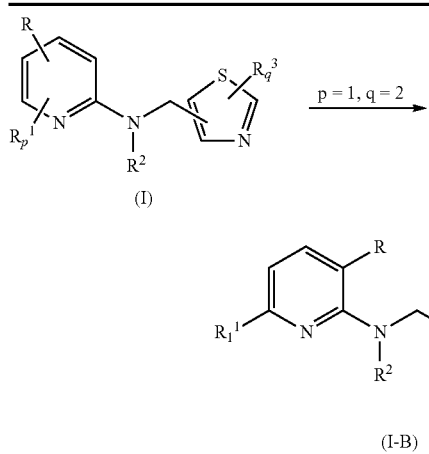

(I) → (I-B), p = 1, q = 2

| No. | R | $R_1^1$ | $R^2$ | $R_1^3$ | $R_2^3$ | m.p.(° C.) |
|---|---|---|---|---|---|---|
| 39 | NO₂ | OCH₃ | CH₃ | CH₃ | CF₃ | 111.2-112.6 |
| 40 | NO₂ | OCH₃ | CH₂CH₃ | CH₃ | CF₃ | Yellow viscous liquid |
| 41 | NO₂ | OCH₂CH₃ | CH₂CH₃ | CH₃ | CF₃ | Yellow viscous liquid |
| 42 | NO₂ | OCH₂CH₃ | CH₃ | CH₃ | CF₃ | Yellow viscous liquid |
| 43 | NO₂ | Cl | CH₂CH₃ | CH₃ | CF₃ | Yellow viscous solid |
| 44 | NO₂ | OCH₃ | CH₂CH₃ | CH₃ | CH₃ | Yellow solid |

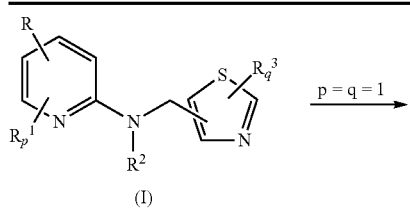

(I) → p = q = 1

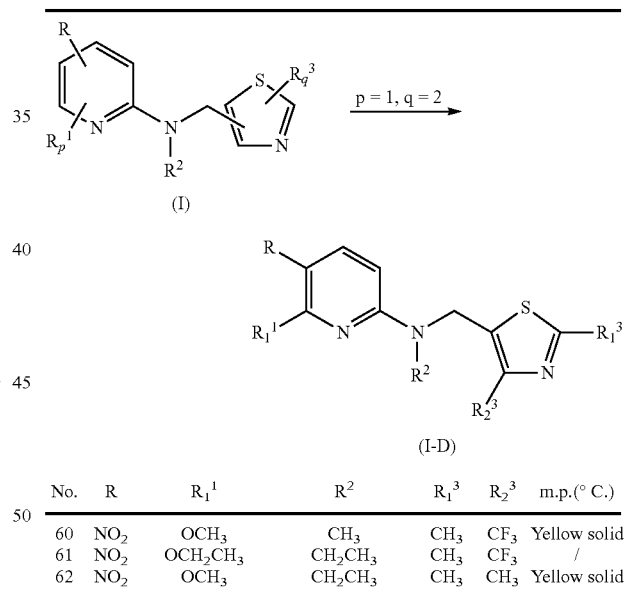

(I) → (I-C), p = 1, q = 2

| No. | R | $R_1^1$ | $R^2$ | $R_1^3$ | m.p.(° C.) |
|---|---|---|---|---|---|
| 45 | NO₂ | OCH₂CH₃ | CH₂CH₃ | Cl | Brown viscous liquid |
| 46 | NO₂ | OCH₂CH₂CH₃ | CH₂CH₂CH₃ | Cl | Brown viscous liquid |
| 47 | NO₂ | OCH₃ | H | Cl | 132.7-138.6 |
| 48 | NO₂ | OCH₃ | CH₂CH₃ | Cl | 127.7-132.0 |
| 49 | NO₂ | NHCH₃ | CH₂CH₃ | Cl | 141.5-144.9 |
| 50 | NO₂ | H | CH₃ | Cl | 162.7-163.5 |
| 51 | NO₂ | OCH₂CH₃ | CH₃ | Br | 130.2-133.7 |
| 52 | NO₂ | OCH₂C≡CH | CH₂CH₃ | Cl | 114.3-115.6 |
| 53 | NO₂ | OCH₂CF₃ | CH₂CH₃ | Cl | 138.2-138.6 |
| 54 | NO₂ | NHCH(CH₃)₂ | CH₂CH₃ | Cl | 142.1-143.8 |
| 55 | NO₂ | N(CH₃)₂ | CH₂CH₃ | Cl | 123.9-124.5 |
| 56 | NO₂ | pyrrolidinyl | CH₂CH₃ | Cl | 153.2-154.5 |
| 57 | NO₂ | N(CH₂CH₃)₂ | CH₂CH₃ | Cl | 79.5-80.5 |
| 58 | NO₂ | CN | CH₂CH₃ | Cl | 115.0-117.1 |
| 59 | NO₂ | Cl | CH₂CH₃ | Cl | Yellow solid |

(I) → (I-D), p = 1, q = 2

| No. | R | $R_1^1$ | $R^2$ | $R_1^3$ | $R_2^3$ | m.p.(° C.) |
|---|---|---|---|---|---|---|
| 60 | NO₂ | OCH₃ | CH₃ | CH₃ | CF₃ | Yellow solid |
| 61 | NO₂ | OCH₂CH₃ | CH₂CH₃ | CH₃ | CF₃ | / |
| 62 | NO₂ | OCH₃ | CH₂CH₃ | CH₃ | CH₃ | Yellow solid |

TABLE 2

| No | ¹H NMR δ (ppm) |
|---|---|
| 01 | (CDCl₃) 1.171 (t, J = 7.2 Hz, 3H, CH₃), 3.165 (q, J = 7.2 Hz, 2H, CH₂), 4.807 (s, 2H, CH₂), 6.783 (d, J = 8.7 Hz, 1H, Py H), 7.503 (s, 1H, Thiazole-H), 8.050 (d, J = 8.7 Hz, 1H, Py H). |
| 02 | (CDCl₃) 4.885 (dd, J = 6.0 Hz, 0.6 Hz, 2H, CH₂), 6.784 (m, 1H, Py H), 7.506 (d, J = 0.6 Hz, 1H, Thiazole-H), 8.445-8.509 (m, 2H, Py H). |
| 03 | (CDCl₃) 1.155 (t, J = 6.9 Hz, 3H, CH₃), 3.139 (q, J = 6.9 Hz, 2H, CH₂), 4.826 (s, 2H, CH₂), 6.819 (dd, J₁ = 4.8 Hz, J₂ = 8.1 Hz, 1H, Py H), 7.479 (s, 1H, Thiazole-H), 8.072 (d, J = 8.1 Hz, 1H, Py H), 8.402 (d, J = 4.8 Hz, 1H, Py H). |
| 04 | (CDCl₃) 1.100 (t, J = 6.9 Hz, 3H, CH₃), 1.322 (t, J = 6.9 Hz, 3H, CH₃), 3.189 (q, J = 6.9 Hz, 2H, CH₂), 4.295 (q, J = 6.9 Hz, 2H, CH₂), 4.754 (s, 2H, CH₂), 6.108 (d, J = 9.0 Hz, 1H, Py H), 7.397 (s, 1H, Thiazole-H), 8.084 (d, J = 9.0 Hz, 1H, Py H). |

TABLE 2-continued

| No | ¹H NMR δ (ppm) |
|---|---|
| 05 | (CDCl$_3$) 1.201 (t, J = 6.9 Hz, 3H, CH$_3$), 3.270 (q, J = 6.9, 2H, CH$_2$), 3.982(s, 3H, CH$_3$), 4.851 (s, 2H, CH$_2$), 6.202 (d, J = 8.7, 1H, Py H), 7.480 (s, 1H, Thiazole-H), 8.159 (d, J = 8.7, 1H, Py H). |
| 06 | (CDCl$_3$) 0.709 (t, J = 7.2 Hz, 3H, CH$_3$), 1.476 (m, 2H, CH$_2$), 3.021 (t, J = 7.8 Hz, 2H, CH$_2$), 4.757 (s, 2H, CH$_2$), 6.758dd, J$_1$ = 4.5 Hz, J$_2$ = 7.8 Hz, 1H, Py H), 7.399 (s, 1H, Thiazole-H), 7.998 (d, J = 8.1 Hz, 1H, Py H), 8.330 (d, J = 7.2 Hz, 1H, Py H). |
| 07 | (CDCl$_3$) 0.940 (t, J = 7.2 Hz, 3H, CH$_3$), 1.119 (t, J = 7.2 Hz, 3H, CH$_3$), 1.617-1.743 (m, 2H, CH$_2$), 3.167-3.234 (q, J = 7.2 Hz, 2H, CH$_2$), 4.220 (t, J = 6.6 Hz, 2H), 4.748 (s, 2H, CH$_2$), 6.111 (d, J = 8.7 Hz, 1H, Py H), 7.393 (s, 1H, Thiazole-H), 8.078 (d, J = 8.7 Hz, 1H, Py H). |
| 08 | (CDCl$_3$) 0.811 (t, J = 7.2 Hz, 3H, CH$_3$), 1.616 (m, 2H, CH$_2$), 3.201 (t, J = 7.5 Hz, 2H, CH$_2$), 3.970 (s, 3H, CH$_3$), 4.832 (s, 2H, CH$_2$), 6.198 (d, J = 8.7 Hz, 1H, Py H), 7.467 (s, 1H, Thiazole-H), 8.155 (d, J = 8.7 Hz, 1H, Py H). |
| 09 | (CDCl$_3$) 0.733 (t, J = 7.2 Hz, 3H, CH$_3$), 1.317 (t, J = 7.2 Hz, 3H, CH$_3$), 1.537 (m, 2H, CH$_2$), 3.115 (t, J = 7.8 Hz, 2H, CH$_2$), 4.307 (q, J = 7.2 Hz, 2H, CH$_2$), 4.734 (s, 2H, CH$_2$), 6.132 (d, J = 9.0 Hz, 1H, Py H), 7.381 (s, 1H, Thiazole-H), 8.076 (d, J = 9.0 Hz, 1H, Py H). |
| 10 | (CDCl$_3$) 0.735 (t, J = 7.2 Hz, 3H, CH$_3$), 0.942 (t, J = 7.2 Hz, 3H, CH$_3$), 1.512 (m, 2H, CH$_2$), 1.721 (m, 2H, CH$_2$), 3.122 (t, J = 7.8 Hz, 2H, CH$_2$), 4.212 (t, J = 6.6 Hz, 2H, CH$_2$), 4.733 (s, 2H, CH$_2$), 6.110 (d, J = 8.7 Hz, 1H, Py H), 7.381 (s, 1H, Thiazole-H), 8.077 (d, J = 8.7 Hz, 1H, Py H). |
| 11 | (CDCl$_3$) 0.862 (t, J = 7.2 Hz, 3H, CH$_3$), 1.241 (m, 2H, CH$_2$), 1.327 (t, J = 7.5 Hz, 3H, CH$_3$), 1.573 (m, 2H, CH$_2$), 3.270 (t, J = 7.5 Hz, 2H, CH$_2$), 4.244 (q, J = 7.2 Hz, 2H, CH$_2$), 4.697 (s, 2H, CH$_2$), 6.134 (d, J = 9.0 Hz, 1H, Py H), 7.283 (s, 1H, Thiazole-H), 8.133 (d, J = 9.0 Hz, 1H, Py H). |
| 12 | (CDCl$_3$) 4.885 (dd, J = 6.0 Hz, 0.9 Hz, 2H, CH$_2$), 6.759 (d, J = 8.4 Hz, 1H, Py H), 7.531 (d, J = 0.9 Hz, 1H, Thiazole-H), 8.394 (d, J = 8.4 Hz, 1H, Py H) |
| 13 | (CDCl$_3$) 2.820 (s, 3H, CH$_3$), 4.830 (s, 2H, CH$_2$), 6.770 (d, J = 8.7 Hz, 1H, Py H), 7.536 (s, 1H, Thiazole-H), 8.099 (d, J = 8.7 Hz, 1H, Py H). |
| 14 | (CDCl$_3$) 4.024 (s, 3H, CH$_3$), 4.911-4.935 (m, 2H, CH$_2$), 6.153 (d, J = 9.0 Hz, 1H, Py H), 7.493 (s, 1H, Thiazole-H), 8.329 (d, J = 9.0 Hz, 1H, Py H). |
| 15 | (CDCl$_3$) 3.173 (d, 3H, CH$_3$), 4.790 (d, J = 3.8 Hz, 2H, CH$_2$), 5.796 (d, J = 9.3 Hz, 1H, Py H), 7.468 (s, 1H, Thiazole-H), 8.209 (d, J = 8.7 Hz, 1H, Py H). |
| 17 | (CDCl$_3$) 2.822 (s, 3H, CH$_3$), 4.007 (s, 3H, CH$_3$), 4.908 (s, 2H, CH$_2$), 6.203 (d, J = 9.0 Hz, 1H, Py H), 7.522 (s, 1H, Thiazole-H), 8.176 (d, J = 9.0 Hz, 1H, Py H). |
| 18 | (CDCl$_3$) 1.197 (t, J = 6.9 Hz, 3H, CH$_3$), 2.572 (s, 3H, CH$_3$), 3.201 (q, J = 6.9 Hz, 2H, CH$_2$), 4.885 (s, 2H, CH$_2$), 6.650 (d, J = 8.7 Hz, 1H, Py H), 7.485 (s, 1H, Thiazole-H), 8.009 (d, J = 8.7 Hz, 1H, Py H). |
| 19 | (CDCl$_3$) 1.297 (t, J = 7.2 Hz, 3H, CH$_3$), 2.826 (s, 3H, CH$_3$), 3.489 (br, 2H, CH$_2$), 4.799 (s, 2H, CH$_2$), 5.879 (d, J = 9.0 Hz, 1H, Py H), 7.504 (s, 1H, Thiazole-H), 8.123 (d, J = 9.0 Hz, 1H, Py H). |
| 20 | (CDCl$_3$) 2.830 (s, 3H, CH$_3$), 3.067 (s, 3H, CH$_3$), 4.825 (s, 2H, CH$_2$), 5.902 (d, J = 9.0 Hz, 1H, Py H), 7.517 (s, 1H, Thiazole-H), 8.142 (d, J = 9.0 Hz, 1H, Py H). |
| 21 | (CDCl$_3$) 1.263 (d, J = 6.6 Hz, 6H, 2*CH$_3$), 2.836 (s, 3H, CH$_3$), 4.055 (br, 1H, CH), 4.800 (s, 2H, CH$_2$), 5.862 (d, J = 9.0 Hz, 1H, Py H), 7.503 (s, 1H, Thiazole-H), 8.121(d, J = 9.0 Hz, 1H, Py H). |
| 22 | (CDCl$_3$) 1.219 (t, J = 7.2 Hz, 3H, CH$_3$), 3.053(s, 3H, CH$_3$), 3.216 (q, J = 7.2 Hz, 2H, CH$_2$), 4.803 (s, 2H, CH$_2$), 5.904 (d, J = 9.0 Hz, 1H, Py H), 7.481 (s, 1H, Thiazole-H), 8.145 (d, J = 9.0 HZ, 1H, Py H). |
| 23 | (CDCl$_3$) 2.825 (s, 3H, CH$_3$), 3.212(s, 6H, 2*CH$_3$), 4.833(s, 2H, CH$_2$), 6.030(d, J = 9.0 Hz, 1H, Py H), 7.271(s, 1H, Thiazole-H), 8.157(d, J = 9.0 Hz, 1H, Py H). |
| 24 | (CDCl$_3$): 1.191(t, J = 7.2 Hz, 3H, CH$_3$), 1.265 (t, J = 7.2 Hz, 3H, CH$_3$), 3.167 (q, J = 7 Hz, 2H, CH$_2$), 3.542 (q, J = 7.2 Hz, 2H, CH$_2$), 4.785 (s, 2H, CH$_2$), 5.200 (br, 1H, NH), 5.888 (d, J = 9.0 Hz, 1H, Py H), 7.473 (s, 1H, Thiazole-H), 8.127 (d, J = 9.0 Hz, 1H, Py H). |
| 25 | (CDCl$_3$) 1.212 (t, J = 7.2 Hz, 3H, CH$_3$), 2.497 (t, J = 2.4 Hz, 1H, CH), 3.265 (q, J = 7.2 Hz, 2H, CH$_2$), 4.850 (s, 2H, CH$_2$), 4.969 (s, 2H, CH$_2$), 6.263 (d, J = 8.7 Hz, 1H, Py H), 7.489 (s, 1H, Thiazole-H), 8.182 (d, J = 8.7 Hz, 1H, Py H). |
| 26 | (CDCl$_3$) 1.208 (t, J = 7.2 Hz, 3H, CH$_3$), 3.299 (q, J = 7.2 Hz, 2H, CH$_2$), 4.721 (q, J = 8.4 Hz, 2H, CH$_2$), 4.795(s, 2H, CH$_2$), 6.331 (d, J = 9.0 Hz, 1H, Py H), 7.476 (s, 1H, Thiazole-H), 8.210 (d, J = 9.0 Hz, 1H, Py H). |
| 27 | (CDCl$_3$) 1.230 (t, J = 7.2 Hz, 3H, CH$_3$), 1.275 (d, 6H, 2*CH$_3$), 3.234 (q, J = 7.2 Hz, 2H, CH$_2$), 4.069 (br, 1H, CH), 4.788 (s, 2H, CH$_2$ ), 5.876 (d, J = 9.0 Hz, 1H, Py H), 7.481 (s, 1H, Thiazole-H), 8.138 (d, J = 9.0 Hz, 1H, Py H). |
| 28 | (CDCl$_3$) 1.193 (t, J = 7.2 Hz, 3H, CH$_3$), 3.192(s, 6H, 2*CH$_3$), 3.216 (q, J = 7.2 Hz, 2H, CH$_2$), 4.811 (s, 2H, CH$_2$), 6.022 (d, J = 9.0 Hz, 1H, Py H), 7.458 (s, 1H, Thiazole-H), 8.165 (d, J = 9.0 Hz, 1H, Py H). |
| 29 | (CDCl$_3$) 1.221 (t, J = 7.2 Hz, 3H, CH$_3$), 3.291 (q, J = 7.2 Hz, 2H, CH$_2$), 4.817(s, 2H, CH$_2$), 4.869 (d, J = 2.7 Hz, 2H, CH$_2$), 5.464-5.267 (m, 2H, CH$_2$), 6.086-5.957 (m, 1H, CH), 6.231 (d, J = 8.7 Hz, 1H, Py H), 7.473 (s, 1H, Thiazole-H), 8.171 (d, J = 8.7 Hz, 1H, Py H). |
| 30 | (CDCl$_3$) 1.104 (t, J = 7.2 Hz, 3H, CH$_3$), 3.127 (q, J = 7.2 Hz, 2H, CH$_2$), 4.546 (s, 2H, CH$_2$), 6.358 (d, J = 8.7 Hz, 1H, Py H), 7.161-7.165 (s, 1H, Thiazole-H), 7.124-7.431 (m, 5H, Ph H) 8.221-8.250 (d, J = 8.7 Hz, 1H, Py H). |
| 31 | (CDCl$_3$) 1.289 (d, J = 6.6 Hz, 6H, 2*CH$_3$), 1.357 (t, J = 6.9 Hz, 3H, CH$_3$), 3.805 (m, 1H, CH), 4.287 (q, J = 6.9 Hz, 2H, CH$_2$), 4.725 (s, 2H, CH$_2$), 6.166 (d, J = 9.0 Hz, 1H, Py H), 7.389 (s, 1H, Thiazole-H), 8.145 (d, J = 9.0 Hz, 1H, Py H). |
| 32 | (CDCl$_3$) 1.193 (t, J = 7.2 Hz, 3H, CH$_3$), 3.182 (q, J = 7.2 Hz, 2H, CH$_2$), 4.829 (s, 2H, CH$_2$), 6.784 (d, J = 8.4 Hz, 1H, Py H), 7.528 (s, 1H, Thiazole-H), 8.049-8.077 (d, J = 8.4 Hz, 1H, Py H). |
| 33 | (CDCl$_3$) 1.00 (t, J = 7.2 Hz, 3H, CH$_3$), 3.256 (q, J = 7.2 Hz, 2H, CH$_2$), 3.982 (s, 3H, CH$_3$), 4.874 (d, J = 1.0 Hz, 2H, CH$_2$), 6.205 (d, J = 9.0 Hz, 1H, Py H), 7.511 (s, 1H, Thiazole-H), 8.206 (d, J = 9.0 Hz, 1H, Py H). |
| 34 | (CDCl$_3$) 1.187(m, 9H, 3*CH$_3$), 3.234(q, J = 7.2 Hz, 2H, CH$_2$), 3.530(q, J = 7.2 Hz, 4H, 2*CH$_2$), 4.769 (s, 2H, CH$_2$), 6.001(d, J = 9.0 Hz, 1H, Py H), 7.446(s, 1H, Thiazole-H), 8.165(d, J = 9.0 Hz, 1H, Py H). |
| 35 | (CDCl$_3$) 1.193(t, J = 7.2 Hz, 3H, CH$_3$), 2.017(m, 4H, 2*CH$_2$), 3.186(q, J = 7.2 Hz, 2H, CH$_2$), 3.554(t, J = 6.9, 4H, 2*CH$_2$), 4.821(s, 2H, CH$_2$), 5.884(d, J = 9.3 Hz, 1H, Py H), 7.459(s, 1H, Thiazole-H), 8.158(d, J = 9.3 Hz, 1H, Py H). |
| 36 | (CDCl$_3$) 1.182(t, J = 7.2 Hz, 3H, CH$_3$), 3.189(q, J = 7.2 Hz, 2H, CH$_2$), 3.668(m, 4H, 2*CH$_2$), 3.784(m, 4H, 2*CH$_2$), 4.779(s, 2H, CH$_2$), 6.082(d, J = 9.0 Hz, 1H, Py H), 7.453(s, 1H, Thiazole-H ), 8.178(d, J = 9.0 Hz, 1H, Py H). |
| 37 | (CDCl$_3$) 1.179 (t, J = 7.2 Hz, 3H, CH$_3$), 3.413 (q, J = 7.2 Hz, 2H, CH$_2$), 4.726 (s, 2H, CH$_2$), 6.378 (d, J = 8.7 Hz, 1H, Py H), 7.447 (s, 1H, Thiazole-H), 7.497 (s, 1H, Thiazole-H). |
| 38 | (CDCl$_3$) 1.202 (t, J = 7.2 Hz, 3H, CH$_3$), 3.418 (q, J = 7.2 Hz, 2H, CH$_2$), 4.033 (s, 3H, CH$_3$), 4.530 (d, J = 0.6 Hz,, 2H, CH$_2$), 6.726 (d, J = 8.1 Hz, 1H, Py H), 7.034 (s, 1H, Thiazole-H), 7.454 (d, J = 8.1 Hz, 1H, Py H). |
| 39 | (CDCl$_3$) 2.674 (s, 3H, CH$_3$), 2.876 (s, 3H, CH$_3$), 3.904 (s, 3H, CH$_3$), 5.143 (s, 2H, CH$_2$), 6.202 (d, J = 8.7 Hz, 1H, Py H), 8.171 (d, J = 8.7 Hz, 1H, Py H). |

TABLE 2-continued

| No | $^1$H NMR δ (ppm) |
|---|---|
| 40 | (CDCl$_3$) 1.232 (t, J = 7.2 Hz, 3H, CH$_3$), 2.641 (s, 3H, CH$_3$), 3.273 (q, J = 7.2 Hz, 2H, CH$_2$), 3.865 (s, 3H, CH$_3$), 5.038 (s, 2H, CH$_2$), 6.207(d, J = 8.7 Hz, 1H, Py H), 8.162(d, J = 9.0 Hz, 1H, Py H). |
| 41 | (CDCl$_3$) 1.209 (t, J = 7.2 Hz, 3H, CH$_3$), 1.287 (t, J = 7.2 Hz, 3H, CH$_3$), 2.636 (s, 3H, CH$_3$), 3.265 (q, J = 7.2 Hz, 2H, CH$_2$), 4.262 (q, J = 7.2 Hz, 2H, CH$_2$), 5.001(s, 2H, CH$_2$), 6.185 (d, J = 8.7 Hz, 1H, Py H), 8.162 (d, J = 8.7 Hz, 1H, Py H). |
| 42 | (CDCl$_3$) 1.320(t, J = 7.2 Hz, 3H, CH$_3$), 2.667(s, 3H, CH$_3$), 2.878(s, 3H, CH$_3$), 4.301 (q, J = 7.2 Hz, 2H, CH$_2$), 5.118 (s, 2H, CH$_2$), 6.179 (d, J = 8.7 Hz, 1H, Py H), 8.166(d, J = 9.0 Hz, 1H, Py H). |
| 43 | (CDCl$_3$) 1.176(t, J = 7.2 Hz, 3H, CH$_3$), 2.663 (s, 3H, CH$_3$), 3.181 (q, J = 7.2 Hz, 2H, CH$_2$), 5.048 (s, 2H, CH$_2$), 6.785(d, J = 8.4 Hz, 1H, Py H), 8.037 (d, J = 8.4 Hz, 1H, Py H). |
| 44 | (CDCl$_3$) 1.199 (t, J = 7.2 Hz, 3H, CH$_3$), 2.383 (s, 3H, CH$_3$), 2.603 (s, 3H, CH$_3$), 3.303 (q, J = 7.2 Hz, 2H, CH$_2$), 3.960 (s, 3H, CH$_3$), 4.778 (s, 2H, CH$_2$), 6.151 (d, J = 8.7 Hz, 1H, Py H), 8.141 (d, J = 9.0 Hz, 1H, Py H). |
| 45 | (CDCl$_3$) 1.099(t, J = 7.2 Hz, 3H, CH$_3$), 1.152(t, J = 7.2 Hz, 3H, CH$_3$), 4.110 (q, J = 7.2 Hz, 2H, CH$_2$), 4.306 (q, J = 7.2 Hz, 2H, CH$_2$), 4.656 (s, 2H, CH$_2$), 6.054 (d, J = 9.0 Hz, 1H, Py H), 7.323 (s, 1H, Thiazole-H), 8.063 (d, J = 8.7 Hz, 1H, Py H). |
| 47 | (CDCl$_3$): 4.104 (s, 3H, CH$_3$), 4.913 (s, 2H, CH$_2$), 6.155 (d, J = 9.0 Hz, 1H, Py H), 7.495 (s, 1H, Thiazole-H), 8.327 (d, J = 9.0 Hz, 1H, Py H). |
| 48 | (CDCl$_3$): 1.226 (t, J = 7.5 Hz, 3H, CH$_3$), 3.488(q, J = 7.5 Hz, 2H, CH$_2$), 4.105 (s, 3H, CH$_3$), 4.913 (s, 2H, CH$_2$), 6.137 (d, J = 8.7 Hz, 1H, Py H), 7.483 (s, 1H, Thiazole-H), 8.309 (d, J = 9.0 Hz, 1H, Py H) |
| 49 | (CDCl$_3$) 1.135(t, J = 6.9 Hz, 3H, CH$_3$), 3.153 (q, J = 6.9 Hz, 2H, CH$_2$), 3.467 (s, 3H, CH$_3$), 4.916 (s, 2H, CH$_2$), 5.957 (d, J = 8.4 Hz, 1H, Py H), 7.488 (s, 1H, Thiazole-H), 8.228 (d, J = 9.3 Hz, 1H, Py H). |
| 50 | (CDCl$_3$) 3.173 (s, 3H, CH$_3$), 4.988 (s, 2H, CH$_2$), 6.531(d, J = 7.8 Hz, 1H, Py H), 7.502 (s, 1H, Thiazole-H), 8.276 (d, J = 7.2 Hz, 1H, Py H), 9.132 (s, 1H, Py H). |
| 52 | (CDCl$_3$) 1.257 (t, J = 7.2 Hz, 3H, CH$_3$), 2.475 (t, J = 2.4 Hz, 1H, CH), 3.505 (q, J = 7.2 Hz, 2H, CH$_2$), 4.945 (s, 2H, CH$_2$), 5.081-5.089 (m, 2H, CH$_2$), 6.182 (d, J = 9.3 Hz, 1H, Py H), 7.490 (s, 1H, Thiazole-H), 8.317 (d, J = 8.7 Hz, 1H, Py H) |
| 53 | (CDCl$_3$) 1.257 (t, J = 7.2 Hz, 3H, CH$_3$), 3.509 (q, J = 7.2 Hz, 2H, CH$_2$), 4.807-4.889(m, 4H, 2*CH$_2$), 6.228 (d, J = 9.0 Hz, 1H, Py H), 7.477 (s, 1H, Thiazole-H), 8.330 (d, J = 9.0 Hz, 1H, Py H). |
| 54 | (CDCl$_3$) 1.206 (t, J = 7.2 Hz, 3H, CH$_3$), 1.297 (m, 6H, 2*CH$_3$), 3.461 (q, J = 7.2 Hz, 2H, CH$_2$), 4.419 (m, 1H, CH), 4.894 (s, 2H, CH$_2$), 5.934 (d, J = 9.0 Hz, 1H, Py H), 7.460 (s 1H, Thiazole-H), 8.232 (d, J = 9.0 Hz, 1H, Py H). |
| 55 | (CDCl$_3$) 1.187 (t, J = 7.2 Hz, 3H, CH$_3$), 3.059(s, 6H, 2*CH$_3$), 3.443 (q, J = 7.2 Hz, 2H, CH$_2$), 4.861 (s, 2H, CH$_2$), 5.959 (d, J = 9.3 Hz, 1H, Py H), 7.267 (s, 1H, Thiazole-H), 8.179 (d, J = 9.0 Hz, 1H, Py H). |
| 56 | (CDCl$_3$) 1,184 (t, J = 7.2 Hz, 3H, CH$_3$), 1.967 (m, 4H, 2*CH$_2$), 3.429 (m, 6H, 3*CH$_2$), 4.860 (s, 2H, CH$_2$), 5.936 (d, J = 9.3 Hz, 1H, Py H), 7.444(s, 1H, Thiazole-H), 8.135(d, J = 9.3 Hz, 1H, Py H). |
| 57 | (CDCl$_3$) 1.189 (m, 9H, 3*CH$_3$), 3.431 (m, 6H, 3*CH$_2$), 4.861 (s, 2H, CH$_2$), 5.948 (d, J = 9.3 Hz, 1H, Py H), 7.268 (s, 1H, Thiazole-H), 8.160 (d, J = 9.0 Hz, 1H, Py H). |
| 58 | (CDCl$_3$) 1.265(t, J = 7.2 Hz, 3H, CH$_3$), 3.561(q, J = 7.2 Hz, 2H, CH$_2$), 4.904 (s, 2H, CH$_2$), 6.741(d, J = 9.9 Hz, 1H, Py H), 7.521 (s, 1H, Thiazole-H), 8.330 (d, J = 9.6 Hz, 1H, Py H). |

The compounds of the present invention represented by the general formula (I) can be prepared through the following scheme 1, scheme 2 and scheme 3, wherein the substituents, unless specially indicated, are the same as previously defined, X' and X are leaving groups, such as halogens (chlorine or bromine) and sulfonates etc.

Scheme 1-1:

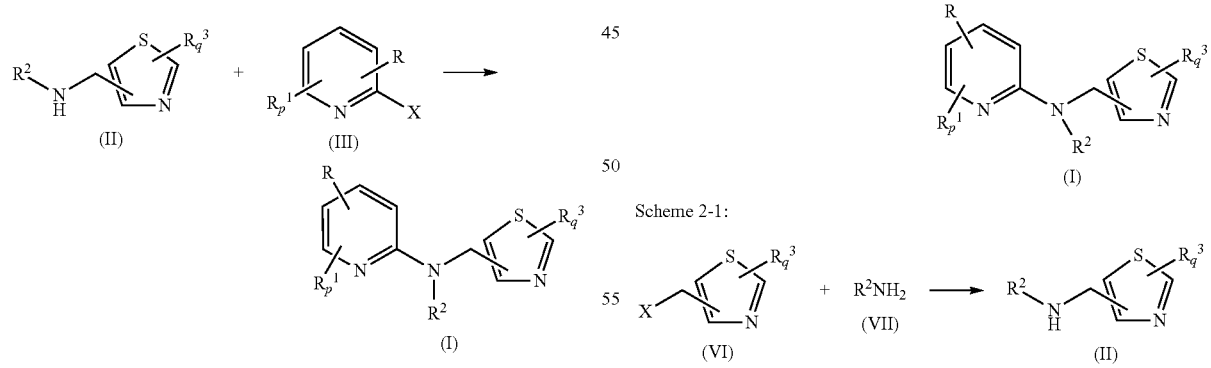

Scheme 1-2:

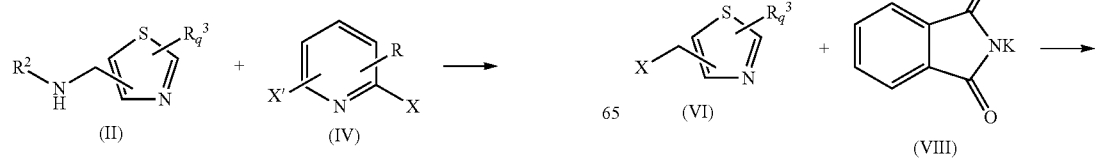

Scheme 2-1:

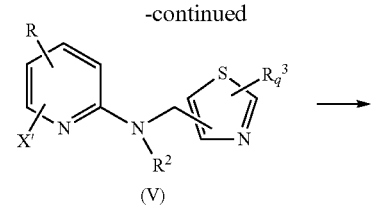

Scheme 2-2:

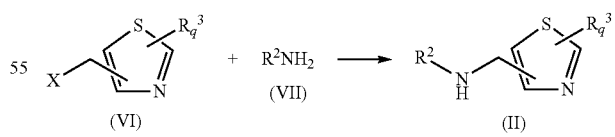

-continued

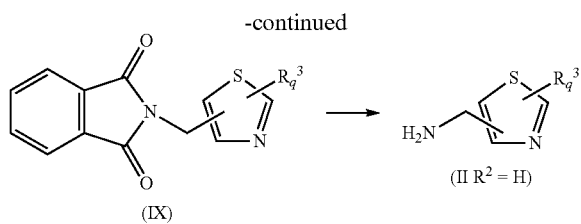

Scheme 2-3:

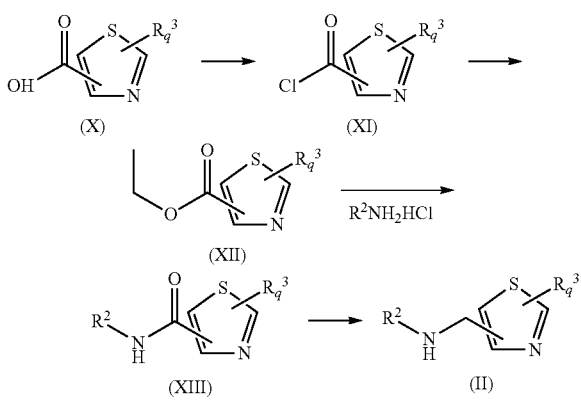

Scheme 3:

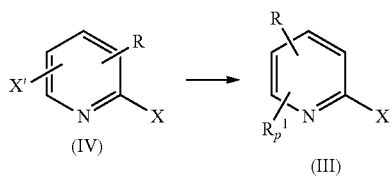

The compounds represented by the general formula (I) can be prepared by the Scheme 1-1. In N,N-dimethylformamide, benzene, toluene or tetrahydrofuran, in the presence of sodium hydride, potassium hydroxide or potassium carbonate, at 25~80° C. or up to the reflux temperature of the solvent used, reacting a compound represented by the general formula (II) with a compound represented by the general formula (III) to give a compound represented by the general formula (I).

The compounds represented by the general formula (I) can also be prepared by the Scheme 1-2 In N,N-dimethylformamide, tetrahydrofuran, water, dichloromethane, benzene or toluene, or in a mixture of two or more of them, in the presence of sodium hydride, potassium hydroxide or potassium carbonate, at room temperature or up to the reflux temperature of the solvent used, reacting a compound represented by the general formula (II) with a compound represented by the general formula (IV) to give a compound represented by the general formula (V), in alcohol or water, metal sodium, sodium alkoxide, or sodium hydride was added when necessary, at room temperature or up to the reflux temperature of the solvent used, reacting a compound represented by the general formula (V) with $R_P^1H$, to give a compound represented by the general formula (I).

The compounds represented by the general formula (II) can be prepared by the Scheme 2-1 In chloroform, dichloromethane, benzene or toluene, or a mixture of it with water or alcohol, in the presence of sodium hydride, sodium hydroxide or potassium carbonate, at room temperature or up to the reflux temperature of the solvent used, reacting a compound represented by the general formula (VI) with a compound represented by the general formula (VII) to give a compound represented by the general formula (II), the addition of a phase transfer catalyst benzyltriethyl ammonium chloride or tetrabutyl ammonium bromide, can promote or accelerate the reaction.

The compounds represented by the general formula (II: $R^2$=H) can also be prepared by the Scheme 2-2 In N,N-dimethylformamide or ethanol, at room temperature or up to the reflux temperature of the solvent used, reacting a compound represented by the general formula (VI) with a compound represented by the general formula (VIII) to give a compound represented by the general formula (IX), in methanol or ethanol, at room temperature or up to the reflux temperature of the solvent used, a compound represented by the general formula (IX) is reduced by hydrazine, hydrazine hydrate or catalytic hydrogenation, to give a compound represented by the general formula (II $R^2$=H).

The compounds represented by the general formula (II) can also be prepared by the Scheme 2-3. Acylating a compound represented by the general formula (X) by thionyl chloride or oxalyl chloride to give a compound represented by the general formula (XI), which reacted with ethanol or methanol to give a compound represented by the general formula (XII), in ethanol or tetrahydrofuran, in the presence of triethylamine, pyridine, potassium carbonate or sodium hydroxide, at 50~160° C., a high-pressure equipment was used when necessary, reacting a compound represented by the general formula (XII) with the hydrochloride salt of a compound represented by the general formula (VII) to give a compound represented by the general formula (XIII), in anhydrous tetrahydrofuran or anhydrous diethyl ether, at the temperature of −10~35° C., a compound represented by the general formula (XIII) is reduced by lithium aluminum hydride or borane to give a compound represented by the general formula (II).

The compounds represented by the general formula (III) can be prepared by the Scheme 3 In the solvent of $R_P^1H$, at −10° C.~the reflux temperature of the solvent used, using $R_P^1ONa$, sodium hydride, sodium hydroxide or potassium carbonate to treat a compound represented by the general formula (IV) to give a compound represented by the general formula (III).

The compounds represented by the general formula (III) can also be prepared by the Scheme 3 In water or N,N-dimethylformamide at −10° C.~the reflux temperature of the solvent used, reacting $R_P^1H$ with a compound represented by the general formula (IV) to give a compound represented by the general formula (III), the addition of triethylamine, sodium hydride, sodium hydroxide or potassium carbonate can promote or accelerate the reaction.

The compounds represented by the general formula (III) can also be prepared by the Scheme 3 In benzene, toluene or petroleum ether, at −10° C.~the reflux temperature of the solvent used, in the presence of sodium hydride, sodium hydroxide or potassium carbonate, reacting $R_P^1H$ with a compound represented by the general formula (IV) to give a compound represented by the general formula (III).

Thiazole methylamino pyridine compounds of the present invention have biological activities, and some have excellent biological activities, especially in the control of diseases in agriculture, horticulture and flower. As mentioned above, diseases include, but are not limited as follows:

Undesirable pathogenic bacteria: *phytophthora* species, *erysiphe* species, *gibberella* species, black star species, *sclerotinia* species, *rhizoctonia* species, *botrytis* species, *pyricularia* species, *fusarium* species, such as *Pyricularia oryzae; Puccinia striiformis, Puccinia recondite* and other *puccinia* diseases; *Erysiphe graminis, Sphaerotheca fuligenea, Podosphaera leucottichar, Podosphaera leucotricha; Septoria nodorum. Helminthosporium,* mouth *neurospora, septoria* diseases, pyrenophorin diseases, *Pseudocercosporella herpotrichoides* and *Gaeumannomyces graminis* generated on cereals. *Cercospora arachidicola* and *Cercosporidium personata*; cercosporamycosis generated on soybeans, sweet bean and rice; *Botrytis cinerea* generated on tomato, cucumber, and grape. *Alternaria* spp. diseases growing on vegetables (such as cucumber); anthracnose on cucumber, scab of apple, cucumber downy mildew, grape downy mildew, diseases generated on potatoes and tomatoes, *Thanatephorus cucumeris* on rice and other *rhizoctonia* on hosts, such as wheat, barley and vegetable; *Sclerotinia sclerotorum, Gibberella zeae*, and *Phytophythora capsici.*

Undesirable insect pests: Orthoptera such as cockroaches, thysanoptera such as *thrips*, rice *thrips*, melon *thrips*, homoptera such as leafhoppers, plant hoppers, aphid, lepidoptera such as the oriental armyworm, *spodoptera*, diamondback moth, cabbage worm, hymenoptera such as sawfly larvae, diptera such as *aedes, culex* mosquitoes, flies, ticks, and mites such as *panonychus citri* and cotton spider mites.

Undesirable weeds: monocot crabgrass weeds, *echinochloa crusgalli, setaria viridis, sclerochloa dura, beckmannia syzigachne, bromus inermis, alopecurus, aegilops tauschii* coss, alkaligrass, *puccinellia tenuiflora*, wild oats, perennial ryegrass; dicotyledonous *abutilon theophrasti* medicus weeds, chickweed, *solanum nigrum, chenopodium quinoa* willd, *amaranthus lividus, amaranthus retroflexus*, and so forth.

As active ingredient of agricultural formulations, thiazole methylamino pyridine compounds of the present invention can be processed into any kind of desired formulations, such as emulsifiable concentrates, wettable powders, suspension concentrates, granules, suitable adjuvants including carriers (diluents) and other adjuvants, such as diffusing agent, emulsifiers, wetting agents, dispersing agents, adhesives, and dispersants.

The present invention also provides methods for preparing compositions previously defined by having the compounds represented by the general formula (I) and at least one carrier mixing together. The composition may comprise a single compound or a mixture of several compounds of the present invention.

The composition according to the present invention preferably contains 1% to 99% (by weight) of the active ingredients. Carriers of the present invention is satisfied by the following conditions: the composition is easy to use in the following treatment after the carrier is mixed with the active ingredients, such as a plant, seeds or soil; or to facilitate the storage, transport or handling. The carriers may be a solid or a liquid, including gaseous but which has been compressed into a liquid bead material, and carriers which are conventionally used in the preparation of insecticidal, acaricidal and fungicidal compositions.

The suitable solid carriers include natural and synthetic clays and silicates, such as diatomaceous, talc, attapulgite clay, aluminum silicate (kaolin), montmorillonites and micas; calcium carbonate; calcium sulphate; ammonium sulphate; synthetic silica, synthetic calcium silicate or aluminum silicates; elements, such as carbon and sulfur; natural and synthetic resins, such as benzofuran resins, polyvinyl chloride and styrene polymers and copolymers; solid polychlorophenols; bitumen; waxes such as bees wax, and paraffin wax.

The suitable liquid carriers include water; alcohols such as isopropanol and ethanol; ketones such as acetone, methyl ethyl ketone and cyclohexyl ketone; ethers; aromatic hydrocarbons such as benzene, toluene and xylene; petroleum fractions such as kerosene and mineral oils; chlorinated hydrocarbons such as carbon tetrachloride, tetrachloroethylene, and including mixtures of the above mentioned liquids.

Fungicidal, insecticidal/acaricidal compositions are typically processed to form concentrations for the use of transportation, wherein they are diluted by the user before application. Small amount of surfactant carriers is helpful to process the dilution. Thus, the compositions according to the present invention preferably have at least one carrier which is a surfactant. If the composition comprises at least two carriers, wherein one is the surfactant.

The surfactant can be an emulsifier, a dispersing agent or a wetting agent, which can be a non-ionic surfactant or an ionic surfactant, such as polyacrylic acids, sodium or calcium salt of the lignin sulphonic acids; condensates of aliphatic acids, aliphatic amines or amides with at least 12 carbon atoms and ethylene epoxide and/or propylene epoxide; glycol, sorbitol, sucrose or pentaerythritol tetrastearate, and the condensates of the above mentioned esters and ethylene epoxide and/or propylene epoxide, sulfates or sulfonates of these condensates; alkali metal or alkaline earth metal salts of sulfate or sulfonate ester containing at least 10 carbon atoms.

The compositions of the present invention are wettable powders, powders, granules and solutions, emulsifiable concentrates, emulsions, suspension concentrates, aerosols and aerosols. Wettable powders usually contain 15, 25, 50% of the active ingredients, and usually not only contain inactive solid carriers, but also contain 3 to 10% of the dispersing agents, and when necessary further adding 0 to 10% of stabilizers or other additives therein, such as the osmotic agents and the adhesive agents. Powders typically have a similar composition to that of a wettable powder without a dispersant. Granules are usually prepared with the size from 10 to 100 mesh (1.676-0.152 mm) and group or injection techniques can be used in its preparation. Generally, granules contain 0.5 to 50% of the active ingredients and 0 to 10% of the additives, such as stabilizers, surfactants, slow-released enhancers. The emulsifiable concentrates not only can be a solvent, when necessary, but also can contain a co-solvent, 1 to 50% W/V of active ingredients, 2 to 20% W/V of emulsifier and 0 to 20% W/V of other additives, such as stabilizers, penetrants and corrosion inhibitors. Suspension concentrates usually contain 10 to 75% of the active ingredient, 0.5 to 15% of dispersing agents, and 0.1 to 10% of other additives, such as deformers, corrosion inhibitors, stabilizers, penetrants and adhesive agents.

The aqueous dispersing agents and emulsions, such as the compositions got by diluting a wettable powder or concentrates of the present invention are also included in the scope of the invention. The emulsions comprise a water-in-oil type and a water-in-oil type.

By adding one or more other acaricides, the composition will have a broader spectrum of activities than the composition only containing the compounds of the present invention do. In addition, other acaricides may have synergistic effects to the compounds of the present invention. There are a lot of acaricides whose active ingredient can be contained in the composition of the present invention, such as aramite, propargite, diafenthiuron, fenpyroximate, hexythiazox, pyridaben, and so forth.

By adding one or more other fungicides, the composition will have a broader spectrum of activities than the composition only containing the compounds of the present invention do. In addition, other fungicides may have synergistic effects to the compounds of the present invention. There are a lot of fungicides whose active ingredient can be contained in the composition of the present invention, such as strobilurin fungicides, benomyl, carbendazim, chlorothalonil, dimethomorph, triadimefon, myclobutanil cyanide, mancozeb and so forth.

By adding one or more other insecticides, the composition will have a broader spectrum of activities than the composition only containing the compounds of the present invention do. In addition, other insecticides may have synergistic effects to the compounds of the present invention. There are a lot of insecticides whose active ingredient can be contained in the composition of the present invention, such as organic phosphorus pesticides methamidophos, phoxim, monocrotophos and imidacloprid, triazamate, indoxacarb as well as synthetic pyrethroids fenvalerate, cyfluthrin, bifenthrin, chlorantraniliprole, flubendiamide and so forth.

DETAILED DESCRIPTION OF THE PREFERRED EMBODIMENT

The present invention is explained in further detail with examples but the present invention is not limited to the following examples unless it exceeds the gist thereof, and the yields in examples are not optimized.

Example 1

Compound No. 01 in Table 1

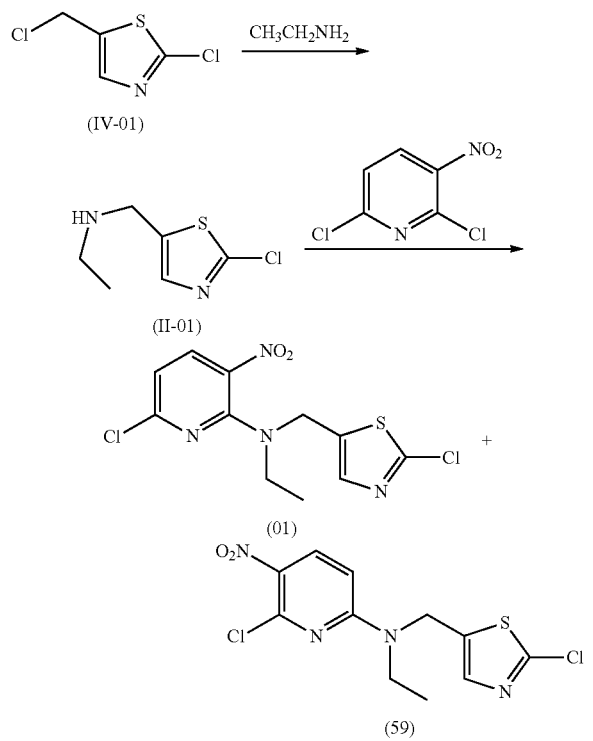

A 60~70% aqueous solution of ethylamine (3.6 mL) and a 20% aqueous NaOH solution (8.0 mL) were added dropwise respectively into a solution of 2-chloro-5-chloromethylthiazole (3.40 g) in chloroform (40 mL), then benzyl triethyl ammonium chloride (0.1 g) was added. After stirring overnight at room temperature, the pH of the resulting mixture was adjusted to weak alkaline. The organic layer was separated while the aqueous layer was extracted with dichloromethane twice. The organic phases were combined, and dried over anhydrous sodium sulfate after washed with an iced aqueous sodium chloride solution twice, then remove the solvent under reduced pressure to obtain 2-chloro-5-ethylaminomethylthiazole 3.37 g as an oil in 95.2% purity. GC-MS: ($M^+$) (EI, 70 eV, m/z) calc: 176. found: 176.

A solution of 2-chloro-5-ethylaminomethylthiazole (2.76 g) in DMF (6.0 mL) was added dropwise to a solution of 2,6-dichloro-3-nitropyridine (3.00 g) and potassium carbonate (4.30 g) in DMF (15 mL). The reaction mixture stirred at 50-80° C. for 3-5 hr. After cooling down, the resulting mixture was added to water (100 mL) and extracted with ethyl acetate, dried over anhydrous sodium sulfate, then remove the solvent under reduced pressure to obtain the residue 4.67 g, which was purified by a silica gel column chromatography using petroleum ether/ethyl acetate (10/1) as an eluent to obtain 6-chloro-N-(2-chlorothiazole-5-yl)methyl-N-ethyl-3-nitropyridine-2-amine 1.36 g, as a golden yellow solid in 98.2% purity. m.p. 71.4-74.1° C., yield 25.7%. GC-MS: ($M^+$) (EI, 70 eV, m/z) calc: 332. found: 332. 1H NMR: (CDCl3/TMS, 300 MHz) δ (ppm) 1.171 (t, J=7.2 Hz, 3H, CH3), 3.165 (q, J=7.2 Hz, 2H, CH2), 4.807 (s, 2H, CH2), 6.783 (d, J=8.7 Hz, 1H, Py H), 7.503 (s, 1H, Thiazole-H), 8.050 (d, J=8.7 Hz, 1H, Py H).

At the same time, a small quantity of 6-chloro-N-(2-chlorothiazole-5-yl)methyl-N-ethyl-5-nitropyridine-2-amine (Compound No. 59 in Table 1) is obtained as a yellow solid in 98.2% purity.

Example 2

Compound No. 04 in the Table 1 (Method A)

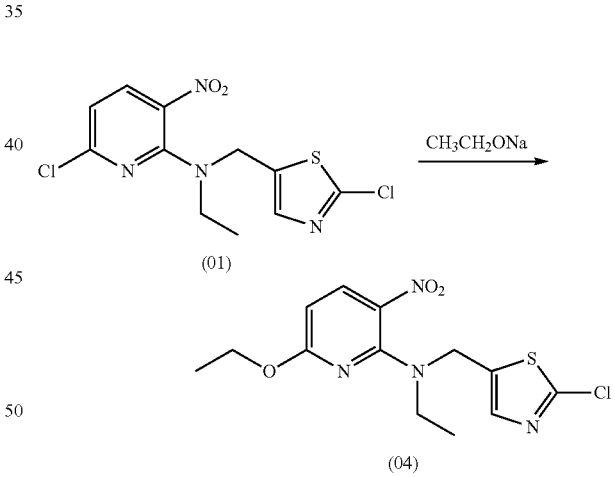

2.30 g of 6-chloro-N-((2-chlorothiazole-5-yl)methyl)-N-ethyl-3-nitropyridine-2-amine (prepared in example 1) in ethanol (5 mL) was added dropwise to 0.16 g of sodium metal in 10 mL of anhydrous ethanol, the reaction mixture stirred at the room temperature for 2 to 6 hours, then treated according to example 1 to obtain 0.68 g of 6-ethoxy-N-((2-chlorothiazole-5-yl)methyl)-N-ethyl-3-nitropyridine-2-amine, at 98.0% purity, as a yellow viscous liquid, yield of 28.2%. GC-MS ($M^+$) (EI, 70 eV, m/z) calc: 342. found: 342. $^1$H NMR (CDCl$_3$/TMS, 300 MHz) δ (ppm) 1.100 (t, J=6.9 Hz, 3H, CH$_3$), 1.322 (t, J=6.9 Hz, 3H, CH$_3$), 3.189 (q, J=6.9 Hz, 2H, CH$_2$), 4.295 (q, J=6.9 Hz, 2H, CH$_2$), 4.754 (s, 2H, CH$_2$), 6.108 (d, J=9.0 Hz, 1H, Py H), 7.397 (s, 1H, Thiazole H), 8.084 (d, J=9.0 Hz, 1H, Py H).

Example 3

Compound No. 04 in Table 1 (Method B)

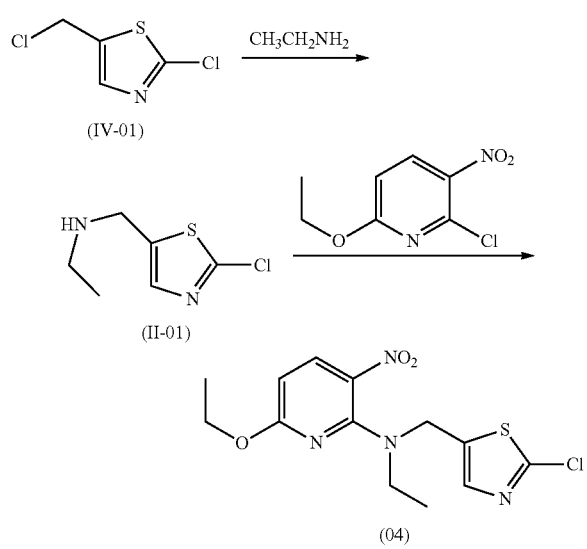

9.6 g of 2,6-dichloro-3-nitropyridine and 60 mL of ethanol were added into a 100 mL three-necked flask equipped with a magnetic stirrer, a constant pressure funnel and a drying tube, after stirred at room temperature for 30 minutes, 3.4 g of sodium ethoxide in 30 ml of ethanol were added dropwise. then the reaction solution was stirred at room temperature for further 2-3 hr, and continuously the resulting mixture was poured into water (100 mL), and then filtered and dried to obtain 9.7 g of light yellow solid, which was confirmed as a mixture with 80% of 2-chloro-6-ethoxy-3-nitropyridine and 20% of 2-ethoxy-6-chloro-3-nitropyridine by a mass spectrometry and $^1$H NMR spectrum. 2-chloro-6-ethoxy-3-nitropyridine and 2-chloro-6-ethoxy-5-nitropyridine were obtained respectively after purification.

1.36 g of 2-chloro-6-ethoxy-3-nitropyridine, 10 mL of N,N-dimethylformamide (DMF), and 2.00 g of potassium carbonate were added to a 100 mL single neck flask, under stirring at room temperature, 1.20 g of 2-chloro-5-ethylaminomethylthiazole prepared in the example 1 in 5.0 mL of DMF was added dropwise. After that, the reaction solution was heated to 40-80° C. and reacted for 3-6 hr. After cooling down, the resulting mixture was added to water (50 mL), then treated by the method according to the example 1 to obtain 1.01 g of 6-ethoxy-N-((2-chlorothiazole-5-yl)methyl)-N-ethyl-3-nitropyridin-2-amine, a viscous liquid, with 98.6% purity, a yield of 43.2%, and the structure was confirmed by GC-Mass and $^1$H NMR.

Example 4

Compound No. 05 in Table 1 (Method A)

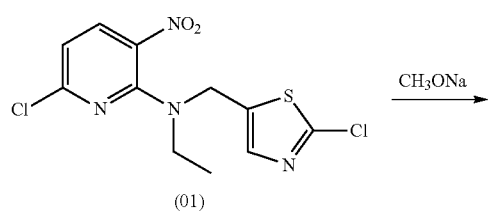

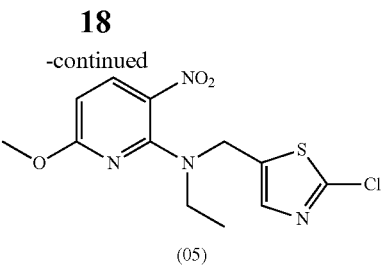

0.16 g of sodium metal and 10 mL of anhydrous methanol were added into a 100 mL three-necked flask equipped with a magnetic stirrer, a condenser and a drying tube, and stirred at reflux temperature until the reaction was complete. Cooling the reaction solution to room temperature, 2.30 g of 6-chloro-N-((2-chlorothiazole-5-yl)methyl)-N-ethyl-3-nitropyridin-2-amine, obtained in the example 1, in 5 mL of methanol was added dropwise at room temperature, and then stirred further 2-6 hr. The reaction solution was treated by the method according to example 1 to obtain 0.59 g of 6-methoxy-N-((2-chlorothiazole-5-yl)methyl)-N-ethyl-3-nitropyridin-2-amine with 98.2% purity, as a golden yellow solid, m.p.: 64.7-66.6° C., yield of 25.7%. GC-MS (M$^+$) (EI, 70 eV, m/z) calc: 328. found: 328. $^1$H NMR (CDCl$_3$/TMS, 300 MHz) δ (ppm) 1.201 (t, J=6.9 Hz, 3H, CH$_3$), 3.270 (q, J=6.9 Hz, 2H, CH$_2$), 3.982 (s, 3H, CH$_3$), 4.851 (s, 2H, CH$_2$), 6.202 (d, J=8.7 Hz, 1H, Py H), 7.480 (s, 1H, Thiazole-H), 8.159 (d, J=8.7 Hz, 1H, Py H).

Example 5

Compound No. 05 in Table 1 (Method B)

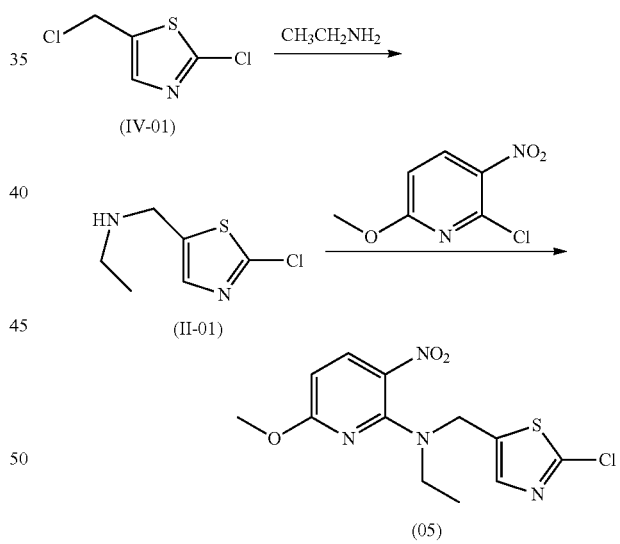

1.26 g 2-chloro-6-methoxy-3-nitropyridine and 10 mL N,N-dimethylformamide (DMF), and 2.00 g of potassium carbonate were added into a 100 mL single neck flask, under stirring at room temperature, 1.20 g of 2-chloro-5-ethylaminomethylthiazole, prepared according to the example 1, in 5.0 mL DMF were added dropwise. After that, the reaction solution was heated to 40-80° C. and then reacted for 3-6 hr. After cooling down, the resulting mixture was added to water (50 mL), then treated by the method according to the example 1 to obtain 1.27 g of 6-methoxy-N-((2-chlorothiazole-5-yl)methyl)-N-ethyl-3-nitropyridine-2-amine, as a golden yellow solid, having the content of 98.6%, a yield of 58.3%, and the structure was confirmed by GC-Mass and $^1$H NMR.

Example 6

Compound No. 14 in Table 1

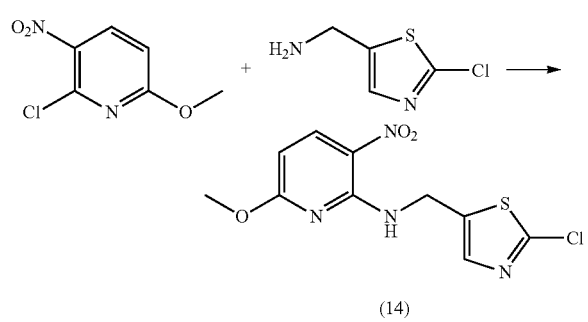

18.5 g of phthalimide potassium salt and 60 mL of N,N-dimethylformamide (DMF) were added into a 100 mL three-necked flask equipped with a magnetic stirrer, a constant pressure dropping funnel and a drying tube. After stirred thoroughly, 16.7 g of 2-chloro-5-chloromethylthiazole in 40 mL of DMF were added dropwise, stirred at the room temperature for 4 to 6 hours, and then the reaction mixture was filtered and dried to obtain 25.3 g off-white solid.

25.3 g of the above mentioned off-white solid and 150 mL of ethanol were added into a 250 mL of three-necked flask equipped with a magnetic stirrer, a condenser and a drying tube, and 9.1 g of hydrazine hydrate was added dropwise. After that, the reaction mixture was refluxed for 4 to 6 hours, and then the solvent was removed under a reduced pressure condition to obtain 9.1 g (2-chlorothiazol-5-yl)methanamine as an orange oil.

1.13 g of 2-chloro-6-methoxy-3-nitropyridine, prepared according to the example 3, and 15 mL of N,N-dimethylformamide, 1.50 g of potassium carbonate were added into a 100 mL single neck flask. Under stirring at room temperature, 0.99 g of (2-chlorothiazol-5-yl)methanamine in 10.0 mL of DMF was added dropwise. After that, the reaction mixture was heated to 50-80° C. and then reacted for 3-5 hr. After cooling down, the resulting mixture was added to ice water (100 mL), and then extracted by ethyl acetate, dried over anhydrous sodium sulfate, concentrated under a reduced pressure to obtain the residue 1.76 g, which was purified by a silica gel column chromatography using petroleum ether/ethyl acetate (5/1) as an eluent to obtain 6-methoxy-N-((2-chlorothiazole-5-yl)methyl)-3-nitropridine-2-amine, having the content of 99.0%, as a golden yellow solid, m.p.: 150.2-151.0° C., yield 25.7% GC-MS (M$^+$) (EI, 70 eV, m/z) calc: 300. found: 300. $^1$H NMR (CDCl$_3$) 4.024 (s, 3H, CH$_3$), 4.911-4.935 (m, 2H, CH$_2$), 6.153 (d, J=9.0 Hz, 1H, Py H), 7.493 (s, 1H, Thiazole-H), 8.329 (d, J=9.0 Hz, 1H, Py H).

Example 7

Compound No. 25 in Table 1

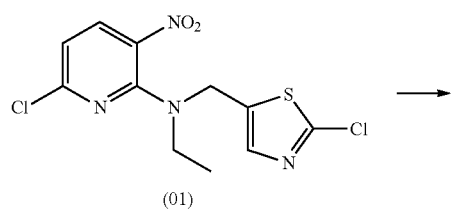

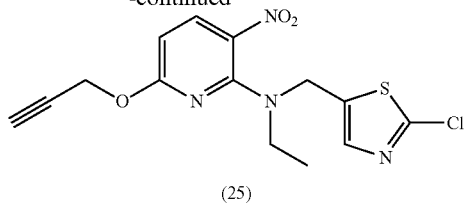

0.52 g of sodium propargyl alcohol and 10 mL of anhydrous dichloromethane were added into a 100 mL three-necked flask equipped with a magnetic stirrer, a condenser and a drying tube, under stirring at room temperature, 1.15 g of 6-chloro-N-((2-chlorothiazole-5-yl)methyl)-N-ethyl-3-nitropyridin-2-amine, prepared according to the example 1, in 5 mL of dichloromethane was added dropwise. After that, the reaction mixture was stirred at room temperature for 1 to 2 hours, and then stirred at reflux temperature for 2 to 5 hours. After cooling down to the room temperature, the reaction mixture was treated by the method according to example 1 to obtain 0.29 g of 6-propargyloxy-N-((2-chlorothiazole-5-yl)methyl)-N-ethyl-3-nitropyridine-2-amine, as a viscous yellow-green solid in a yield of 23.8%. GC-MS (M$^+$) (EI, 70 eV, m/z) calc: 352. found: 352. $^1$H NMR (CDCl$_3$/TMS, 300 MHz) δ (ppm): (CDCl$_3$) 1.212 (t, J=7.2 Hz, 3H, CH$_3$), 2.497 (t, J=2.4 Hz, 1H, CH), 3.265 (q, J=7.2 Hz, 2H, CH$_2$), 4.850 (s, 2H, CH$_2$), 4.969 (s, 2H, CH$_2$), 6.263 (d, J=8.7 Hz, 1H, Py H), 7.489 (s, 1H, Thiazole-H), 8.182 (d, J=8.7 Hz, 1H, Py H).

Example 8

Compound No. 28 in Table 1

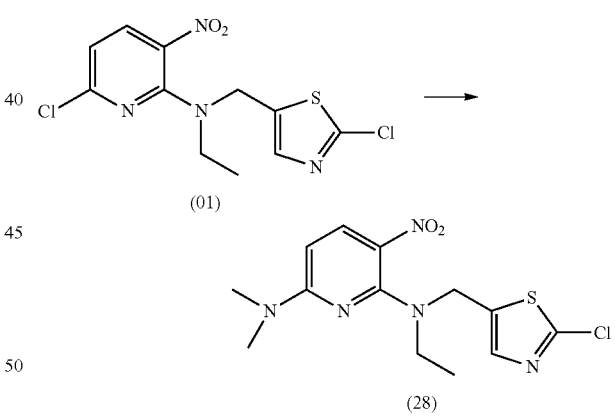

1.15 g of 33% aqueous dimethylamine solution, 10 mL of N,N-dimethylformamide (DMF) and 2.80 g of 6-chloro-N-((2-chloro-thiazol-5-yl)methyl)-N-ethyl-3-nitropyridin-2-amine, prepared according to the example 1, in 5 mL of DMF were added into a 100 mL three-necked flask equipped with a magnetic stirrer, a condenser and a drying tube, under stirring at room temperature, 1.40 g of potassium carbonate was added in batches. Reacted at the room temperature until the reaction was complete. The reaction solution was treated by the method according to example 1 to obtain 0.92 g of 6-dimethylamino-N-((2-chlorothiazole-5-yl)methyl)-N-ethyl-3-nitropyridine-2-amine, the content of 98.0%, as a golden yellow solid in a yield of 31.4%, mp: 74.6-78.4° C., GC-MS (M$^+$) (EI, 70 eV, m/z) calc: 341. found: 341. $^1$H NMR (CDCl$_3$/

TMS, 300 MHz) δ (ppm) 1.193 (t, J=7.2 Hz, 3H, CH₃), 3.192 (s, 6H, 2*CH₃), 3.216 (q, J=7.2 Hz, 2H, CH₂), 4.811 (s, 2H, CH₂), 6.022 (d, J=9.0 Hz, 1H, Py H), 7.458 (s, 1H, thiazole-H), 8.165 (d, J=9.0 Hz, 1H, Py H).

Example 9

Compound No. 29 in Table 1

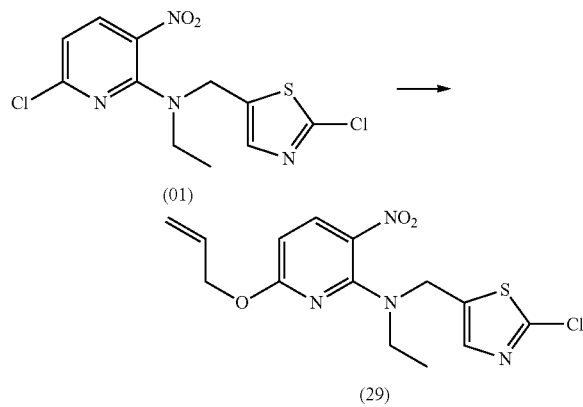

1.10 g of 6-chloro-N-((2-chlorothiazole-5-yl)methyl)-N-ethyl-3-nitropyridine-2-amine, prepared according to the example 1, in 30 mL of DMF was added into a 100 mL three-necked flask equipped with a magnetic stirrer, a condenser and a drying tube, under stirring at 5-10° C., 1.02 g of sodium prop-2-en-1-olate (the content of 30.7%) in 20 mL of DMF was added dropwise, and the reaction was complete after further stirred for 4 to 6 hours. The reaction mixture was treated by the method according to the example 1 to obtain 0.25 g of 6-allyloxy-N-((2-chlorothiazole-5-yl)methyl)-N-ethyl-nitropyridine-2-amine, having the content of 91%, as a brown sticky solid in a yield of 19.4%. GC-MS (M⁺) (EI, 70 eV, m/z) calc: 354. found: 354. ¹H NMR (CDCl₃/TMS, 300 MHz) δ (ppm) 1.221 (t, J=7.2 Hz, 3H, CH₃), 3.291 (q, J=7.2 Hz, 2H, CH₂), 4.817 (s, 2H, CH₂), 4.869 (d J=2.7 Hz, 2H, CH₂), 5.464-5.267 (m, 2H, CH₂), 6.086-5.957 (m, 1H, CH), 6.231 (d, J=8.7 Hz, 1H, Py H), 7.473 (s, 1H, Thiazole-H), 8.171 (d, J=8.7 Hz, 1H, Py H).

Example 10

Compound No. 33 in Table 1

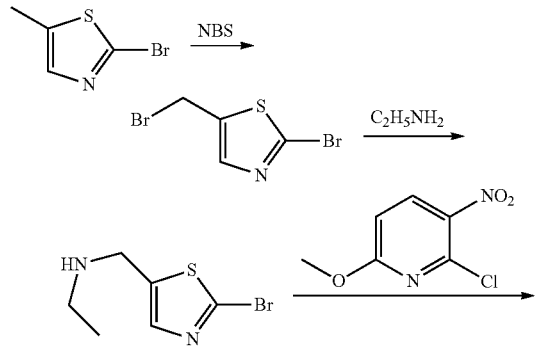

-continued

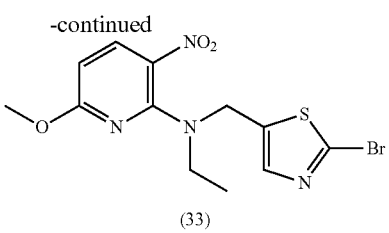

11.8 g of 2-bromo-5-methylthiazole, 18.85 g of N-bromosuccinicimide (NBS), 42.4 mg of azobisisobutyronitrile (AIBN), and carbon tetrachloride (150 mL), were added into a 250 mL single-neck flask equipped with a magnetic stirrer, and, the reaction mixture was stirred at reflux temperature for 20 to 30 hours. After cooling down, the reaction mixture was extracted by carbon tetrachloride. The organic layer was separated while the aqueous layer was extracted with carbon tetrachloride twice. The organic phases were combined, and dried over anhydrous sodium sulfate after washed with an iced aqueous sodium chloride solution twice, then remove the solvent under reduced pressure to obtain 13.8 g of 2-bromo-5-bromomethylthiazole which was used in the next reaction directly without purification.

2-bromo-5-ethylaminomethylthiazole is prepared according to the method for 2-chloro-5-ethylaminomethylthiazole in the example 1.

6-methoxy-N-((2-bromothiazole-5-yl)methyl)-N-ethyl-3-nitropyridine-2-amine was prepared according to the method for 6-ethoxy-N-((2-chlorothiazole-5-yl)methyl)-N-ethyl-3-nitropyridin-2-amine according to the example 3, having the content of 95.0%, as a viscous liquid. GC-MS (M⁺) (EI, 70 eV, m/z) calc: 372. found: 372. ¹H NMR (CDCl₃/TMS, 300 MHz) δ (ppm) 1.00 (t, J=7.2 Hz, 3H, CH₃), 3.256 (q, J=7.2 Hz, 2H, CH₂), 3.982 (s, 3H, CH₃), 4.874 (d, J=1.0 Hz, 2H, CH₂), 6.205 (d, J=9.0 Hz, 1H, Py H), 7.511 (s, 1H, Thiazole-H), 8.163 (d, J=9.0 Hz, 1H, Py H).

Example 11

Compound No. 37 in Table 1

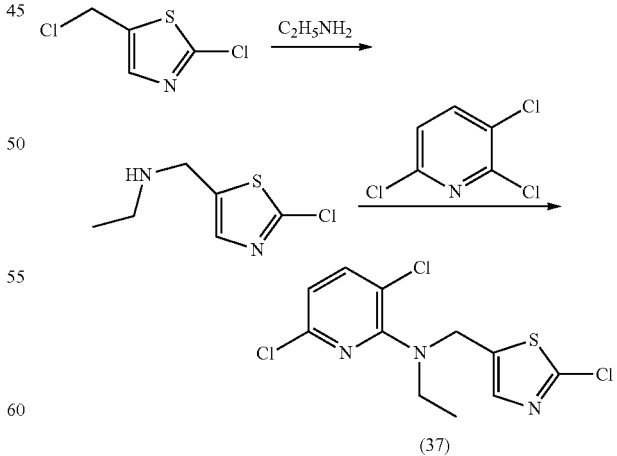

18.0 g of 2-chloro-5-ethylaminomethylthiazole, 18.6 g of 2,3,6-trichloropyridine, 30.0 g of potassium carbonate and 200 mL of N,N-dimethylformamide (DMF) were added in a 500 mL single neck flask equipped with a magnetic stirrer.

After stirred at reflux temperature for 4 to 6 hours, the reaction mixture was extracted with ethyl acetate, the organic layer was separated while the aqueous layer was extracted with ethyl acetate twice. The organic phases were combined, and dried over anhydrous sodium sulfate after washed with an iced aqueous sodium chloride solution twice, then remove the solvent under reduced pressure to obtain 25.0 g of crude product which was purified by a silica gel column chromatography using a petroleum ether/ethyl acetate (20/1) as an eluent to obtain 13.0 g of 6-chloro-N-((2-chlorothiazole-5-yl)methyl)-N-ethyl-3-chloropyridin-2-amine, having the content 91.0%, as a yellow viscous liquid, and rod-like crystals were generated after standing, m.p.: 95.8-96.8 □ GC-MS (M$^+$) (EI, 70 eV, m/z) calc: 321. found: 321. $^1$H NMR (CDCl$_3$/TMS, 300 MHz) δ (ppm) 1.179 (t, J=7.2 Hz, 3H, CH$_3$), 3.413 (q, J=7.2 Hz, 2H, CH$_2$), 4.726 (s, 2H, CH$_2$), 6.378 (d, J=8.7 Hz, 1H, Py H), 7.447 (d, J=8.7 Hz, 1H, Py H), 7.497 (s, 1H, Thiazole-H).

Example 12

Compound No. 38 in Table 1

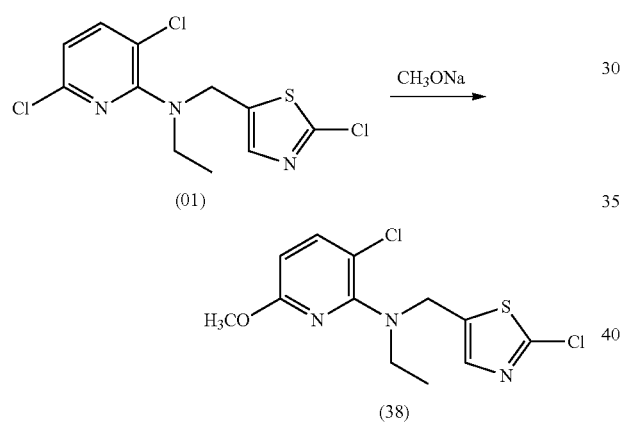

(38)

1.5 g of 6-chloro-N-((2-chlorothiazole-5-yl)methyl)-N-ethyl-3-chloropyridine-2-amine, prepared according to the example 11, and 20 mL of tetrahydrofuran were added in a 150 mL single neck flask equipped with a magnetic stirrer, after stirred at room temperature for 10 to 30 minutes, 0.25 g of sodium methoxide in 2.0 mL of methanol were added dropwise. The reaction mixture was stirred at the same temperature overnight, and then extracted with ethyl acetate, the organic layer was separated while the aqueous layer was extracted with ethyl acetate twice. The organic phases were combined, and dried over anhydrous sodium sulfate after washed with an iced aqueous sodium chloride solution twice, then remove the solvent under reduced pressure to obtain 1.20 g of crude product which was purified by a silica gel column chromatography using a petroleum ether/ethyl acetate (15/1) as an eluent to obtain 0.42 g of 6-methoxy-N-((2-chlorothiazole-5-yl)methyl)-N-ethyl-3-chloropyridin-2-amine, having the content of 95.0% as a yellow viscous liquid, GC-MS (M$^+$) (EI: 70 eV, m/z) calc: 317. found: 317. $^1$H NMR (CDCl$_3$/TMS, 300 MHz) δ (ppm) 1.202 (t, J=7.2 Hz, 3H, CH$_3$), 3.418 (q, J=7.2 Hz, 2H, CH$_2$), 4.033 (s, 3H, CH$_3$), 4.530 (d, J=0.6 Hz, 2H, CH$_2$), 6.726 (d, J=8.1 Hz, 1H, Py H), 7.034 (s, 1H, Thiazole-H), 7.454 (d, J=8.1 Hz, 1H, Py H).

Example 13

Compound No. 44 in Table 1

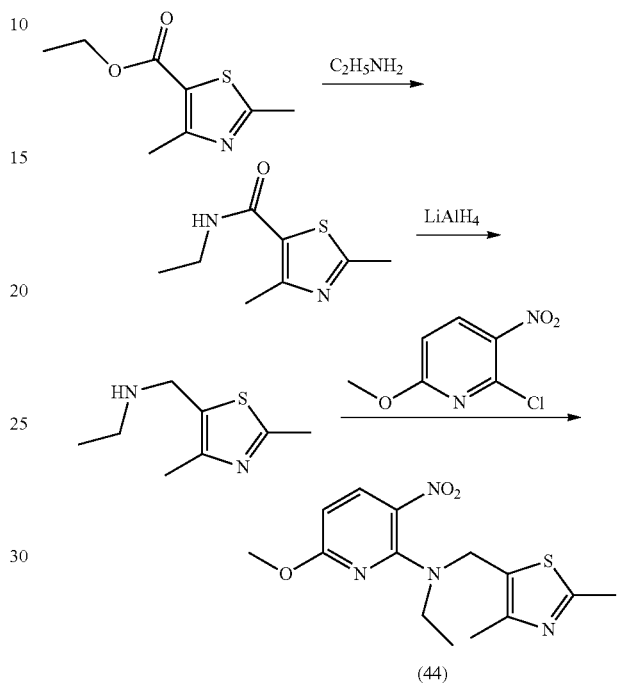

(44)

3.0 g of ethyl 2,4-dimethylthiazole-5-carboxylate, 7.0 g of ethylamine hydrochloride, 6.0 g of triethylamine, and 100 mL of ethanol were added into a 250 mL of high-pressure reactor. And the reaction mixture was heated to 120-160° C. and stirred for 20 to 30 hours, and then extracted with ethyl acetate, the organic layer was separated while the aqueous layer was extracted with ethyl acetate twice. The organic phases were combined, and dried over anhydrous sodium sulfate after washed with an iced aqueous sodium chloride solution twice, then remove the solvent under reduced pressure to obtain 1.5 g N-ethyl-2,4-dimethylthiazole-5-carboxamide which was used in the next step directly without purification.

0.8 g of lithium aluminum hydride and 20 mL of tetrahydrofuran were added in a 150 mL of single-neck flask equipped with a magnetic stirrer. After stirred for 0.5 to 1.0 hour under ice bath cooling, 1.5 g of N-ethyl-2,4-dimethylthiazole-5-carboxamide in 10 mL of tetrahydrofuran solution are added dropwise, and reacted at the same temperature for 0.5 to 10 hours, and then for 1 to 2 hours at room temperature. The reaction mixture was then extracted with ethyl acetate, the organic layer was separated while the aqueous layer was extracted with ethyl acetate twice. The organic phases were combined, and dried over anhydrous sodium sulfate after washed with an iced aqueous sodium chloride solution twice, then remove the solvent under reduced pressure to obtain 1.0 g of 2,4-dimethyl-5-ethylaminomethylthiazole which was used in the next step directly without purification.

1.0 g of 2,4-dimethyl-5-ethylaminomethylthiazole, 1.5 g of 2-chloro-3-nitro-6-methoxypyridine, 5.0 g of potassium carbonate, 20 mL of N,N-dimethylformamide (DMF) were added into a 150 mL of single-neck flask equipped with a magnetic stirrer. And the reaction mixture was stirred at room temperature overnight. And then extracted with ethyl acetate, the organic layer was separated while the aqueous layer was extracted with ethyl acetate twice. The organic phases were combined, and dried over anhydrous sodium sulfate after washed with an iced aqueous sodium chloride solution twice, then remove the solvent under reduced pressure to obtain 1.5 g of crude product which was purified by a silica gel column chromatography using a petroleum ether/ethyl acetate (20/1) as an eluent to obtain 0.49 g of 6-methoxy-N-(2,4-dimethylthiazole-5-yl)methyl)-N-ethyl-3-nitropyridine-2-amine, having the content of 98%, as a yellow viscous liquid, and solidified after standing. GC-MS (M+) (EI, 70 eV, m/z) calc: 322. found: 322. $^1$H NMR (CDCl$_3$/TMS, 300 MHz) δ (ppm) 1.199 (t, J=7.2 Hz, 3H, CH$_3$), 2.383 (s, 3H, CH$_3$), 2.603 (s, 3H, CH$_3$), 3.303 (q, J=7.2 Hz, 2H, CH$_2$), 3.960 (s, 3H, CH$_3$), 4.778 (s, 2H, CH$_3$), 6.151 (d, J=8.7 Hz, 1H, Py H), 8.141 (d, J=9.0 Hz, 1H, Py H).

Example 14

Compound No. 45 in Table 1

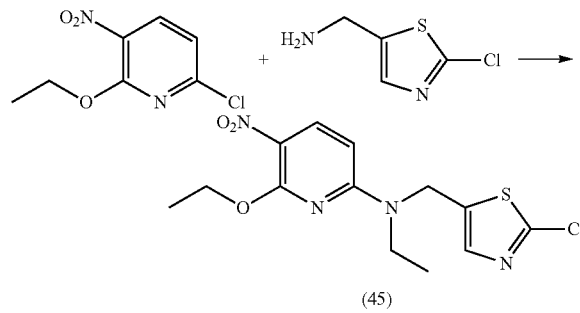

(45)

2.7 g of sodium hydride and 80 mL of toluene were added into a 250 mL of three-neck flask equipped with a magnetic stirrer, a constant pressure dropping funnel and a drying tube. After stirred for 20 to 30 minutes under the ice bath cooling condition, 2.4 g of ethanol in 10 mL of toluene was added dropwise, and stirred at the same temperature for 30 to 45 minutes. And then 10.0 g of 2,6-dichloro-3-nitropyridine in 40 mL of toluene were added dropwise and stirred for further 2 to 4 hours at room temperature, then the water was added, and the reaction mixture was extracted by toluene, the organic layer was separated and dried, then remove the solvent under reduced pressure to obtain 9.8 g as an orange liquid, which was confirmed as 98% of 2-ethoxy-6-chloro-3-nitropyridine and 2% of 2-chloro-6-ethoxy-3-nitropyridine by GC-MS and $^1$H NMR. 2-ethoxy-6-chloro-3-nitropyridine was obtained after separation and purification.

1.0 g of 2-ethoxy-6-chloro-3-nitropyridine, 1.4 g of potassium carbonate and 20 mL of N,N-dimethylformamide (DMF) were added into a 100 mL three-neck flask equipped with a magnetic stirrer, a constant pressure dropping funnel and a drying tube. After stirred for 20 to 30 minutes at room temperature, 0.9 g of 2-chloro-5-ethylaminomethylthiazole in 10 mL of DMF was added dropwise. The reaction solution was heated to 50-80° C. and reacted for 2 to 6 hours. After cooling down, the resulting mixture was added to ice water and extracted with ethyl acetate, dried over anhydrous sodium sulfate, then remove the solvent under reduced pressure to obtain the residue 4.67 g, which was purified by a silica gel column chromatography using petroleum ether/ethyl acetate (10/1) as and then the reaction solution was cooled down by pouring the iced water therein. The reaction solution was extracted by ethyl acetate, and the organic layer was separated and dried, then the solvent was removed under reduced pressure to obtain a crude product. The crude product was purified by a silica gel column chromatography using a petroleum ether/ethyl acetate (5/1) as an eluent to obtain 2-ethoxy-N-((2-chlorothiazole-5-yl)methyl)-N-ethyl-3-nitropyridine-5-amine. GC-MS (M+) (EI, 70 eV, m/z) calc: 322. found: 322. $^1$H NMR (CDCl$_3$/TMS, 300 MHz) δ (ppm) 1.099 (t, J=7.2 Hz, 3H, CH$_3$), 1.152 (t, J=7.2 Hz, 3H, CH$_3$), 4.110 (q, J=7.2 Hz, 2H, CH$_2$), 4.306 (q, J=7.2 Hz, 2H, CH$_2$), 4.656 (s, 2H, CH$_2$), 6.054 (d, J=9.0 Hz, 1H, Py H), 7.323 (s, 1H, Thiazole-H), 8.063 (d, J=8.7 Hz, 1H, Py H).

Example 15

The preparation of emulsifiable concentrate (EC): 20 parts (by weight) of a thiazolylmethylpyridin-amine compound provided by the invention, 73 parts of diluents, such as xylene, and 7 parts of suitable additive are mixed thoroughly to give an emulsifiable concentrate which can be used after being diluted with water (the content of active compound is 20%).

Example 16

The preparation of 20% EC of compound 05, 6-methoxy-N-((2-chlorothiazole-5-yl)methyl)-N-ethyl-3-nitropyridin-2-amine: 20 parts of the compound 05 (by weight), 73 parts of diluents, such as xylene and 7 parts of suitable additives are mixed thoroughly to give 20% EC of No. 05 which can be used after being diluted with water (the content of active compound is 20%).

Example 17

The preparation of wettable powders: 20 parts (by weight) of a thiazolylmethylpyridin-amine compound provided by the invention, 53 parts of clay, 20 parts of white carbon, 5 parts of lignin silicate, and 2 parts of polyoxyethylene alkyl ether are grounded into a fine powder and mixed thoroughly to give a wettable powder (the content of active compound is 20%).

The fungicidal, insecticidal, acaricidal and herbicidal activities of the synthesized compounds are bioassayed, and the parts of the experiment results are listed as followings.

Example 18

Fungicidal Activity Against *Sclerotonia Sclerotiorum*

Bioassay method: Stock solution of every test compound was prepared in an appropriate solvent such as N,N-dimethylformamide (DMF), and then diluted to the required test concentrations with sterile water containing 0.1% Tween 80; Pipetted 3 mL of test solution to 27 mL of potato dextrose agar (PDA) medium at 45° C. and poured into a Petri dish to prepare a plate after shaking thoroughly; 6 mm of diameter of fungi cake from the edge of 7-day-old bacterial colony was inoculated on the central of the plate, wherein mycelium facing down, and cultured in the culture tank at 28° C. The diameter of fungi spread was calculated 4 days later using the control group tested with the diluent only. Test was run 4 times. Data were subjected to EXCEL statistical software analysis and the growth inhibition of the tested compound was calculated according to the corresponding control, the activity was rated on the basis of percentage of growth inhibition using the following rating system: A, inhibition (%)>90; B, 90≥inhibition (%)>70; C, 70≥inhibition (%)>50; D, inhibition (%)≤50. Some of the test results are shown in Table 3 to Table 5.

TABLE 3

The activities against *Sclerotinia sclerotiorum* of some compounds at 25 mg/L (%)

| Compound | 04 | 05 | 07 | 08 | 09 | 10 | 25 | 28 | 29 | 33 | 44 |
|---|---|---|---|---|---|---|---|---|---|---|---|
| Activity | A | A | B | A | A | B | A | A | A | A | A |

TABLE 4

The activities against *Sclerotinia sclerotiorum* of some compounds at 1.25~10 mg/L (%)

| Compound | 10 mg/L | 5 mg/L | 2.5 mg/L | 1.25 mg/L |
|---|---|---|---|---|
| 04 | 100 | 90 | 75 | / |
| 05 | 100 | 100 | 99 | 95 |
| 25 | 96 | 90 | 84 | 78 |
| 28 | 90 | 82 | 64 | 42 |
| 29 | 83 | 79 | 72 | 63 |
| 33 | 100 | 100 | 91 | / |
| 44 | 87 | 75 | 70 | / |

TABLE 5

The activities against *Sclerotinia sclerotiorum* of some compounds at 0.15~5 mg/L (%)

| Compound | 5 mg/L | 2.5 mg/L | 1.255 mg/L | 0.625 mg/L | 0.3125 mg/L | 0.1562 mg/L |
|---|---|---|---|---|---|---|
| 04 | 75 | 70 | 65 | 61 | 59 | 53 |
| 05 | 96 | 90 | 73 | 68 | 63 | 63 |
| Thiophanate-Methyl | 85 | 77 | 72 | 63 | 47 | 33 |
| Procymidone | 93 | 79 | 76 | 66 | 63 | 34 |

Example 19

Fungicidal Activity Against *Botrytis Cinerea*

Fungicidal activities against *Botrytis cinerea* of compounds represented by the general formula (I) were evaluated with the corresponding method in Example 18, and some of the test results are shown in Table 6 to Table 8.

TABLE 6

The activities against *Botrytis cinerea* of some compounds at 25 mg/L (%)

| | Compound | | | | | | | |
|---|---|---|---|---|---|---|---|---|
| | 04 | 05 | 07 | 08 | 09 | 10 | 18 | 23 |
| Activity | A | A | B | A | A | B | B | B |
| | Compound | | | | | | | |
| | 24 | 25 | 28 | 29 | 31 | 33 | 44 | 47 |
| Activity | B | A | A | A | B | B | A | C |

TABLE 7

The activities against *Botrytis cinerea* of some compounds at 1.25~10 mg/L (%)

| Compound | 10 mg/L | 5 mg/L | 2.5 mg/L | 1.25 mg/L |
|---|---|---|---|---|
| 04 | 94 | 78 | 70 | / |
| 05 | 100 | 97 | 92 | 89 |
| 07 | 68 | 52 | 44 | / |
| 08 | 70 | 70 | 68 | / |
| 09 | 65 | 65 | 52 | / |
| 25 | 97 | 93 | 90 | 85 |
| 28 | 96 | 91 | 86 | 79 |
| 29 | 80 | 73 | 67 | 62 |

TABLE 8

The activities against *Botrytis cinerea* of some compounds and commercial fungicides at 0.15~5 mg/L (%)

| Compound | 5 mg/L | 2.5 mg/L | 1.255 mg/L | 0.625 mg/L | 0.3125 mg/L | 0.1562 mg/L |
|---|---|---|---|---|---|---|
| 04 | 90 | 87 | 82 | 81 | 76 | 63 |
| 05 | 100 | 98 | 94 | 88 | 84 | 78 |
| Thiophanate-Methyl | 100 | 98 | 93 | 88 | 75 | 18 |
| Procymidone | 100 | 93 | 83 | 75 | 67 | 46 |

Example 20

Fungicidal Activity Against *Alternaria Alternata*

Fungicidal activities against *Alternaria alternata* of compounds represented by the general formula (I) were evaluated with the corresponding method in Example 18, and some of the test results are shown in Table 9 to Table 10.

TABLE 9

The activities against *Alternaria alternata* of some compounds at 25 mg/L (%)

| Compound | 04 | 05 | 07 | 08 | 17 | 25 | 44 |
|---|---|---|---|---|---|---|---|
| Activity | B | B | C | C | B | B | B |

TABLE 10

The activities against *Alternaria alternata* of some compounds at 2.5~10 mg/L (%)

| Compound | 10 mg/L | 5 mg/L | 2.5 mg/L |
|---|---|---|---|
| 04 | 70 | 60 | 55 |
| 05 | 81 | 75 | 45 |
| 07 | 45 | 36 | 20 |
| 08 | 60 | 48 | 45 |

Example 21

Fungicidal activities against *Alternaria solani, Fusarium oxysporum, Marssonina coronaria, Sphaceloma ampelinum,* Apple canker, *Cercospora arachidicola* and *Alternaria mali* etc of compounds represented by the general formula (I) were evaluated with the corresponding method in Example 18, the results indicated that some compounds showed excellent activity against one or more of them. For example Compound No. 05 showed better than or equal to that of the commercial fungicide Procymidone. Some of the results are shown in Table 11.

TABLE 11

The activities against some Pathogenic bacteria of compound 05 at 25 mg/L (%)

| | Pathogenic bacteria | | | | | |
|---|---|---|---|---|---|---|
| | Cercospora arachidicola | Alternaria mali | Sphaceloma ampelinum | Marssonina coronaria | Fusarium oxysporum | Alternaria solani |
| 05 | 88 | 82 | 93 | 78 | 38 | 87 |
| Procymidone | 85 | 82 | 96 | 75 | 38 | 94 |

Example 22

Acaricidal Activity Against *Tetranychus Urticae*

Bioassay method: Stock solution of every test compound was prepared in an appropriate solvent such as N,N-dimethylformamide, and a small amount of Tween 80 was added as emulsification agent, then diluted to the required test concentrations with distilled water, using the control group tested with distilled water only. 100 to 200 adults of *Tetranychus urticae* were transferred to well-growing horsebean seedlings and 24 hr later, horsebean seedlings with *Tetranychus urticae* were dipped in the test solution for 10 s, then allowed to dry with filter paper and transplanted to the beaker containing water and kept in a room for normal cultivation. Each assay contained three replications, and results were averaged. Mortality was assessed 24 hr after the treatment. The activity was rated on the basis of mortality using the following rating system: A, mortality>90; B, 90≥mortality>70; C, 70≥mortality>50; D, mortality≤50. Some of the test results are shown in Table 12.

TABLE 12

The activities against *Tetranychus urticae* of some compounds at 500 mg/L (%)

| Compound | 25 | 29 | 30 | 47 |
|---|---|---|---|---|
| Activity | C | C | B | B |

Example 23

Insecticidal Activity Against *Aphis Fabae*

Bioassay method: Stock solution of every test compound was prepared in an appropriate solvent such as N,N-dimethylformamide, and a small amount of Tween 80 was added as emulsification agent, then diluted to the required test concentrations with distilled water, using the control group tested with distilled water only. More than 20 adults of *Aphis fabae* were transferred to newly unearthed horsebean seedlings and 24 hr later, horsebean seedlings with *Aphis fabae* were dipped in the test solution for 5 s, then allowed to dry with filter paper, transplanted to the absorbent sponge and covered with a glass tube, then kept in a room for normal cultivation. Each assay contained three replications, and results were averaged. Mortality was assessed 24 hr after the treatment. The activity was rated to A, B, C or D according to the rating system in Example 22. Some of the test results are shown in Table 13 to Table 14.

TABLE 13

The activities against *Aphis fabae* of some compounds at 500 mg/L (%)

| Compound | 04 | 05 | 06 | 07 | 08 | 09 | 10 | 11 | 17 | 45 | 46 |
|---|---|---|---|---|---|---|---|---|---|---|---|
| Activity | A | A | A | A | A | A | A | A | A | B | A |

TABLE 14

The activities against *Aphis fabae* of some compounds at 6.25~100 mg/L (%)

| Compound | 100 mg/L | 25 mg/L | 6.25 mg/L |
|---|---|---|---|
| 04 | 46.7 | 26.7 | 0 |
| 05 | 87.5 | 46.5 | 12.7 |
| 06 | 72.9 | 66.2 | 35.2 |
| 08 | 84.2 | 54.1 | 16.8 |
| 09 | 78.1 | 66.2 | 42.2 |
| 17 | 93.8 | 65.0 | 48.7 |

Example 24

The Evaluation of Herbicidal Activity

Bioassay method: (1) Plastic pots (about 64 cm$^2$) were filled with soil and placed in a stainless steel basin, seeds with the same size and plumpness of monocotyledonous weeds such as *Digitaria sanguinalis, Echinochloa crus-galli, Setaria viridis* and Dicotyledonous weeds such as *Abutilon theophrasti* or *Stelleria media* or *Solanum nigrum, Chenopodium album, Amaranthus ascedene* or *Amaranthus retroflexus* were sown in one-third of the pot area with the soil depth of 1 cm in two different pots separately and grown to the desired leaf stage in a greenhouse wherein water is added to the stainless steel basin until the full infiltration of soils from the bottom of pots; (2) Test compounds represented by the general formula (I) were formulated by using N,N-dimethylformamide as solvent and a small amount of Tween 80 as emulsification agent, then diluted to the required test concentrations with water, using the control group tested with corresponding solvent and water only; (3) the required test solutions were applied for pre-emergence treatment 24 hr after the weeds were sown, for postemergence treatment, monocotyledonous weeds were treated at the 1-leaf stage and dicotyledonous weeds were treated at 2 leaf stage; (4) the pre- and postemergence application rates were 150 g a.i./mu, using the control group with corresponding solvent or water respectively; (5) Treatments were kept in greenhouse for cultivation; (6) Herbicidal activities were evaluated visually 15 to 25 days after treatment, on the basis of the survey results, the weed control effect can be calculated by the following formula: efficacy (%)=(the height of the weed in the control group−the height of the weed in the test group) (the height of the weed in the control group). Parts of the results are shown in Table 15.

TABLE 15

| | The herbicidal activities of some compounds at 150 g a.i./mu (%) | | | | | |
|---|---|---|---|---|---|---|
| | Pre-emergence | | | | | |
| Compound | Abutilon | Amaranthus spinosus | Chenopodium album | Digitaria sanguinalis | Echinochloa crus-galli | Setaria viridis |
| 18 | 0 | 0 | 0 | 90 | 80 | 80 |
| 20 | 70 | 90 | 90 | 70 | 70 | 70 |
| 23 | 70 | 80 | 80 | 0 | 0 | 0 |

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A N-thiazolylmethylpyridin-amine compound, represented by the formula (I):

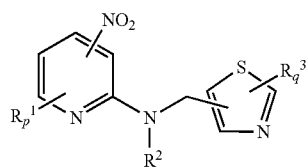

(I)

wherein:
I. p is 0, 1, 2 or 3;
II. q is 0, 1 or 2;
III. $R^1$ represents hydrogen, halogen, cyano group, alkyl group, alkoxy group, alkylthio group, alkenyl group, alkenoxy group, alkenylsulfenyl group, alkynyl group, alkynyloxy group, alkynylsulfenyl group, cycloalkyl group, cycloalkoxy group, cycloalkylthio group, $NR^4R^5$ ($R^4$ and $R^5$ are the same or different, and they represent hydrogen, alkyl group);
$R^2$ represents hydrogen, alkyl group, alkenyl group, alkynyl group, cycloalkyl group;
$R^3$ represents hydrogen, halogen, cyano group, alkyl group, alkoxy group, alkylthio group, alkenyl group, alkenoxy group, alkenylsulfenyl group, alkynyl group, alkynyloxy group, alkynylsulfenyl group, cycloalkyl group, cycloalkoxy group, cycloalkylthio group, $NR^4R^5$ ($R^4$ and $R^5$ are the same or different, and they represent hydrogen, alkyl group);
as mentioned in III, one or more hydrogen atoms in $R^1$, $R^2$ or $R^3$ may be substituted by the same or different following substituent:
halogens, alkyl group, alkenyl group, alkynyl group, cycloalkyl group, alkoxy group, alkylthio group, halo-alkyl group, halo-alkenyl group, halo-alkynyl group, halo-alkynyloxy group, halo-alkynyl group, cycloalkoxy group, cycloalkylthio group, halo-cycloalkyl group;

according to the definition of formula (I), the terms used either alone or in compound words, represent the following substituents:

halogen: represent fluorine, chlorine, bromine or iodine;

alkyl group: represents a $C_1$-$C_6$ straight-chain or branched-chain alkyl group;

alkoxy group: represents a $C_1$-$C_6$ straight-chain or branched-chain alkoxy group attached to the structure by oxygen atom;

alkylthio group: represents a $C_1$-$C_6$ straight-chain or branched-chain alkylthio group attached to the structure by sulfur atom;

alkenyl group: represents a $C_2$-$C_6$ straight-chain or branched-chain alkenyl group;

alkynyl group: represents a $C_2$-$C_6$ straight-chain or branched-chain alkynyl group;

halo-: represents one, a plurality of, or all of the hydrogen atoms are substituted by halogens.

2. The N-thiazolylmethylpyridin-amine compound, as recited in claim 1, wherein in the formula (I):

p is 1; q is 0 or 1; wherein $R^1$ represents hydrogen, halogens, $C_1$~$C_3$ alkyl group, $C_1$~$C_3$ alkoxy group, $C_1$~$C_3$ alkylthio group, $C_2$~$C_6$ alkenyl group, $C_2$~$C_6$ alkenoxy group, $C_2$~$C_6$ alkenylthio group, $C_2$~$C_6$ alkynyl group, $C_2$~$C_6$ alkynyloxy group, $C_2$~$C_6$ alkynylsulfenyl group, $C_3$~$C_6$ cycloalkyl group, $C_3$~$C_6$ cycloalkoxy group, $C_3$~$C_6$ cycloalkylthio group, or $NR^4R^5$ ($R^4$ and $R^5$ are the same or different and they represent $C_1$~$C_3$ alkyl), $R^2$ represents hydrogen, $C_1$~$C_3$ alkyl group, $C_2$~$C_6$ alkenyl group, $C_2$~$C_6$ alkynyl group, $C_3$~$C_6$ cycloalkyl group; $R^3$ represents hydrogen, halogens, $C_1$~$C_3$ alkyl group, $C_1$~$C_3$ alkoxy group, $C_1$~$C_3$ alkylthio group, $C_2$~$C_6$ alkenyl group, $C_2$~$C_6$ alkenoxy group, $C_2$~$C_6$ alkenylthio group, $C_2$~$C_6$ alkynyl group, $C_2$~$C_6$ alkynyloxy group, $C_2$~$C_6$ alkynylsulfenyl group, $C_3$~$C_6$ cycloalkyl group, $C_3$~$C_6$ cycloalkoxy group, $C_3$~$C_6$ cycloalkylthio group, or $NR^4R^5$ ($R^4$ and $R^5$ are the same or different and they represent $C_1$~$C_3$ alkyl), when necessary, hydrogen atoms in $R^1$, $R^2$ or $R^3$ may be substituted partially or entirely by the same or different following substituents: halogen, $C_1$~$C_3$ alkyl group, $C_2$~$C_6$ alkenyl group, $C_2$~$C_6$ alkynyl, $C_3$~$C_6$ cycloalkyl, $C_1$~$C_3$ alkoxy group, $C_1$~$C_3$ alkylthio group.

3. The N-thiazolylmethylpyridin-amine compound, as recited in claim 1, wherein in the formula (I):

p is 1; q is 0 or 1; $R^1$ is $C_1$~$C_3$ alkoxy group, $C_3$~$C_6$ alkenoxy group, $C_3$~$C_6$ alkynyloxy group or $NR^4R^5$ ($R^4$ and $R^5$ are the same or different, and they represent $C_1$~$C_3$ alkyl); $R^2$ is $C_1$~$C_3$ alkyl group or $C_1$~$C_3$ haloalkyl group; $R^3$ is halogens, $C_1$~$C_3$ alkyl group or $C_1$~$C_3$ halo-alkyl group.

4. The N-thiazolylmethylpyridin-amine compound, according to claim 1, wherein in the formula (I):
p is 1; q is 0 or 1; $R^1$ is methoxy group, ethoxy group, allyloxy group, propargyloxy group or $N(CH_3)_2$; $R^2$ is methyl group or ethyl group; $R^3$ is chloro, bromo, methyl group or trifluoromethyl group.

5. The N-thiazolylmethylpyridin-amine compound, as recited in claim 1, wherein the formula (I) represents:
- 6-chloro-N-((2-chlorothiazole-5-yl)methyl)-N-ethyl-3-nitropyridin-2-amine;
- 6-methoxy-N-((2-chlorothiazole-5-yl)methyl)-N-ethyl-3-nitropyridin-2-amine;
- 6-ethoxy-N-((2-chlorothiazole-5-yl)methyl)-N-ethyl-3-nitropyridin-2-amine;
- 6-propargyloxy-N-((2-chlorothiazole-5-yl)methyl)-N-ethyl-3-nitropyridin-2-amine;
- 6-dimethylamino-N-((2-chlorothiazole-5-yl)methyl)-N-ethyl-3-nitropyridin-2-amine;
- 6-allyloxy-N-((2-chlorothiazole-5-yl)methyl)-N-ethyl-3-nitropyridin-2-amine;
- 6-chloro-N-((2-chlorothiazole-5-yl)methyl)-N-methyl-3-nitropyridin-2-amine;
- 6-methoxy-N-((2-chlorothiazole-5-yl)methyl)-N-methyl-3-nitropyridin-2-amine;
- 6-ethoxy-N-((2-chlorothiazole-5-yl)methyl)-N-methyl-3-nitropyridin-2-amine;
- 6-propargyloxy-N-((2-chlorothiazole-5-yl)methyl)-N-methyl-3-nitropyridin-2-amine;
- 6-dimethylamino-N-((2-chlorothiazole-5-yl)methyl)-N-methyl-3-nitropyridin-2-amine;
- 6-allyloxy-N-((2-chlorothiazole-5-yl)methyl)-N-methyl-3-nitropyridin-2-amine;
- 6-chloro-N-((2-bromothiazole-5-yl)methyl)-N-ethyl-3-nitropyridin-2-amine;
- 6-methoxy-N-((2-bromothiazole-5-yl)methyl)-N-ethyl-3-nitropyridin-2-amine;
- 6-ethoxy-N-((2-bromothiazol-5-yl)methyl)-N-ethyl-3-nitropyridin-2-amine;
- 6-propargyloxy-N-((2-bromothiazole-5-yl)methyl)-N-ethyl-3-nitropyridin-2-amine;
- 6-dimethylamino-N-((2-bromothiazole-5-yl)methyl)-N-ethyl-3-nitropyridin-2-amine;
- 6-allyloxy-N-((2-bromothiazole-5-yl)methyl)-N-ethyl-3-nitropyridin-2-amine;
- 6-chloro-N-((2-bromothiazole-5-yl)methyl)-N-methyl-3-nitropyridin-2-amine;
- 6-methoxy-N-((2-bromothiazole-5-yl)methyl)-N-methyl-3-nitropyridin-2-amine;
- 6-ethoxy-N-((2-bromothiazole-5-yl)methyl)-N-methyl-3-nitropyridin-2-amine;
- 6-propargyloxy-N-((2-bromothiazole-5-yl)methyl)-N-methyl-3-nitropyridin-2-amine;
- 6-dimethylamino-N-((2-bromothiazole-5-yl)methyl)-N-methyl-3-nitropyridin-2-amine;
- 6-allyloxy-N-((2-bromothiazole-5-yl)methyl)-N-methyl-3-nitropyridin-2-amine;
- 6-propoxy-N-((2-chlorothiazole-5-yl)methyl)-N-ethyl-3-nitropyridin-2-amine;
- 6-ethoxy-N-((2-chlorothiazole-5-yl)methyl)-3-nitropyridin-2-amine;
- 6-methoxy-N-((2-chlorothiazole-5-yl)methyl)-3-nitropyridin-2-amine;
- 6-methoxy-N-((2,4-dimethylthiazole-5-yl)methyl)-N-ethyl-3-nitropyridin-2-amine;
- 6-methoxy-N-((2-methyl-4-trifluoromethylthiazole-5-yl)methyl)-N-ethyl-3-nitropyridin-2-amine;
- 6-ethoxy-N-((2,4-dimethylthiazole-5-yl)methyl)-N-ethyl-3-nitropyridin-2-amine;
- 6-ethoxy-N-((2-methyl-4-trifluoromethylthiazole-5-yl)methyl)-N-ethyl-3-nitropyridin-2-amine;
- 6-methylthio-N-((2-chlorothiazole-5-yl)methyl)-N-ethyl-3-nitropyridin-2-amine;
- 6-methylthio-N-((2-chlorothiazole-5-yl)methyl)-N-methyl-3-nitropyridin-2-amine;
- 6-methoxy-N-((2-chlorothiazole-5-yl)methyl)-N-propyl-3-nitropyridin-2-amine;
- 6-ethoxy-N-((2-chlorothiazole-5-yl)methyl)-N-propyl-3-nitropyridin-2-amine;
- 6-propoxy-N-((2-chlorothiazole-5-yl)methyl)-N-methyl-3-nitropyridin-2-amine;
- 6-methoxy-N-(thiazole-5-yl)methyl-N-ethyl-3-nitropyridin-2-amine.

* * * * *